US012749189B1

(12) United States Patent
Straka et al.

(10) Patent No.: US 12,749,189 B1
(45) Date of Patent: Sep. 29, 2026

(54) DYNAMIC GENERATION OF A COLLECTION OF BLOOD VESSEL RENDERINGS

(71) Applicant: iSchemaView, Inc., Menlo Park, CA (US)

(72) Inventors: Matus Straka, Winterthur (CH); Roland Bammer, Carlton (AU); Juan Montoya, Arlington, VA (US); Sangaiah Shivkumar Amarnath Yennu, Aurora, CO (US); Benjamin L. Odry, West New York, NJ (US)

(73) Assignee: SchemaView, Inc., Menlo Park, CA (US)

( * ) Notice: Subject to any disclaimer, the term of this patent is extended or adjusted under 35 U.S.C. 154(b) by 0 days.

(21) Appl. No.: 19/543,756

(22) Filed: Feb. 18, 2026

Related U.S. Application Data

(60) Provisional application No. 63/909,714, filed on Oct. 31, 2025.

(51) Int. Cl.

| | |
|---|---|
| ***G16H 50/20*** | (2018.01) |
| ***G06T 7/00*** | (2017.01) |
| ***G06T 7/62*** | (2017.01) |
| ***G06T 15/08*** | (2011.01) |

(52) U.S. Cl.
CPC .............. *G06T 7/0012* (2013.01); *G06T 7/62* (2017.01); *G06T 15/08* (2013.01); *G16H 50/20* (2018.01); *G06T 2207/10081* (2013.01); *G06T 2207/10088* (2013.01); *G06T 2207/20081* (2013.01); *G06T 2207/20084* (2013.01); *G06T 2207/30008* (2013.01); *G06T 2207/30096* (2013.01); *G06T 2207/30104* (2013.01)

(58) Field of Classification Search
CPC ......... G06T 7/0012; G06T 7/62; G06T 15/08; G06T 2207/10081; G06T 2207/10088; G06T 2207/20081; G06T 2207/20084; G06T 2207/30008; G06T 2207/30096; G06T 2207/30104; G16H 50/20
See application file for complete search history.

(56) References Cited

U.S. PATENT DOCUMENTS

2026/0060593 A1 * 3/2026 Van Dam ............... A61B 5/367

FOREIGN PATENT DOCUMENTS

JP 2019165923 A * 10/2019

* cited by examiner

*Primary Examiner* — Said M Elnoubi
(74) *Attorney, Agent, or Firm* — Schwegman Lundberg & Woessner, P.A.

(57) ABSTRACT

Implementations are described directed to providing a comprehensive suite of views of blood vessels located in a body part. For example, the views can include three-dimensional and two-dimensional renderings of blood vessels in the head and neck of a patient. The views can be dynamically manipulated based on user input to show different perspectives of the blood vessels and to switch between different modes of presentation for the blood vessels. The views being rendered can aid a practitioner in identifying abnormalities that are present in blood vessels and can be used to determine treatment protocols for patients.

22 Claims, 7 Drawing Sheets

DYNAMIC GENERATION OF A COLLECTION OF BLOOD VESSEL RENDERINGS

CLAIM OF PRIORITY

This patent application claims the benefit of priority to U.S. provisional patent application No. 63/909,714, filed Oct. 31, 2025, and entitled, “Analyzing Imaging Data To Generate User Interfaces Displaying Modified Images Of Blood Vessels,” which has been incorporated by reference herein in its entirety.

BACKGROUND

Damage can occur to tissue in the human body (including tissue of the blood vessel itself) when blood flow is disrupted to the tissue or altered from its normal physiologic pattern. Decreased or altered blood flow to tissue can have a number of causes, such as blood vessel blockage (e.g., occlusion), rupture of blood vessels or a bulge (e.g., an aneurysm), separation of the different layers of blood vessels (e.g., dissection), constriction of blood vessels (e.g., stenosis), shelf-like protrusions (e.g., a web), or compression of blood vessels (e.g., impingement). The severity of the damage to the tissue can depend on the extent of the blood flow reduction to the tissue and the amount of time that blood flow to the tissue is reduced or entirely disrupted. Tissue damage can be temporary, permanent, and, in some cases, may result in loss of life for the patient.

In situations where blood supply to tissue is inadequate for a prolonged period of time, the tissue may become infarcted. Infarcted tissue represents irreversibly damaged cells of the tissue due to the lack of sufficient blood supply to meet its metabolic demand. Abnormal blood flow patterns can exert more stress on vessel walls, leading to increased bulges and eventually to ruptures, or lead to zones of stagnant blood that can aggregate and form blood clots (e.g., thrombi) which can lead to occlusions further downstream. Prompt identification of areas of the brain in which blood flow has decreased or altered can help to reduce damage to tissue and minimize morbidity and mortality.

BRIEF DESCRIPTION OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some implementations are illustrated by way of example, and not limitation.

DETAILED DESCRIPTION

Figure 1:
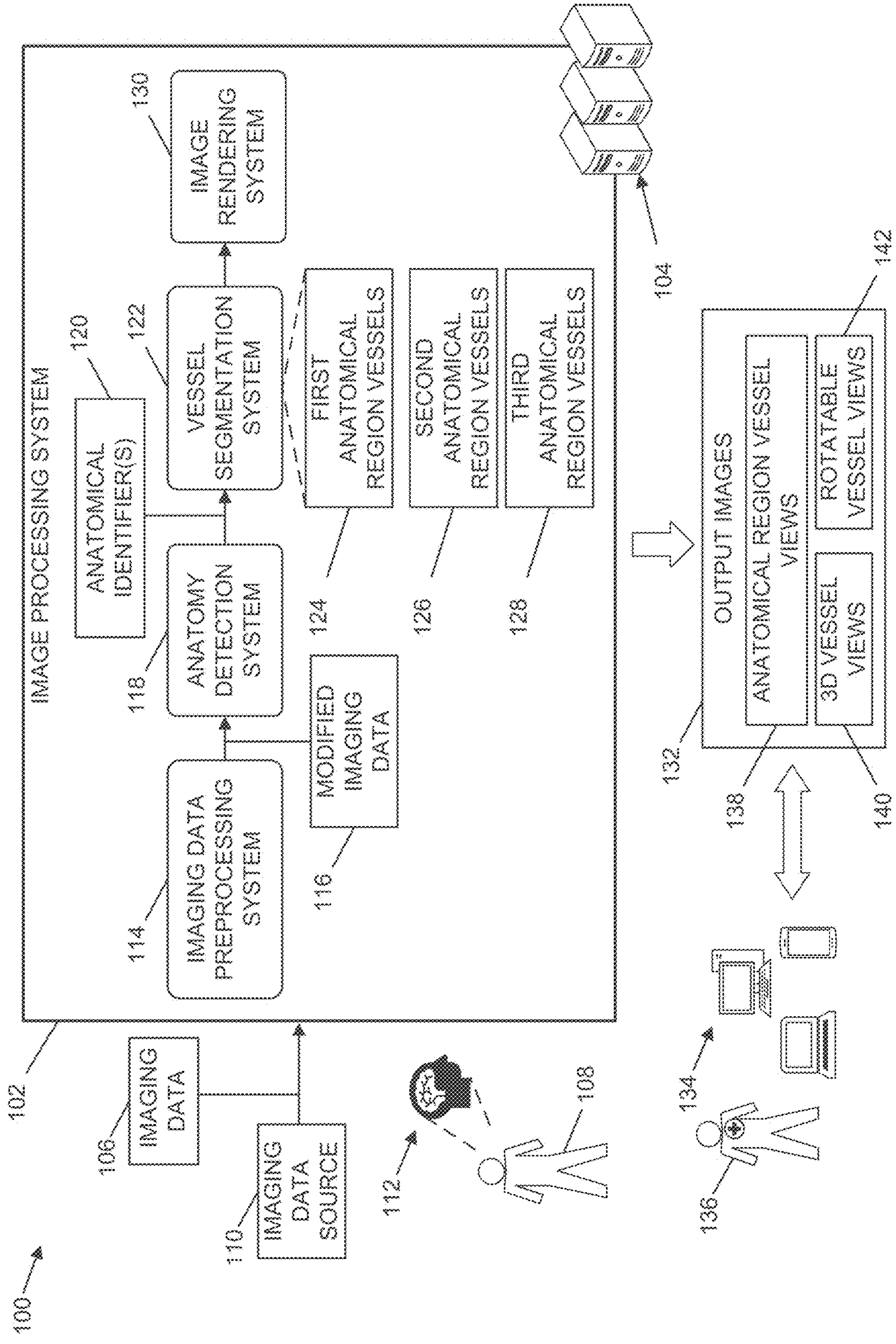
FIG. 1 is a diagrammatic representation of a computational architecture to analyze imaging data to generate a number of images indicating vessels included in different anatomical regions of the head and neck of patients, according to one or more example implementations.

Accurately identifying a location of the brain where a reduction or frank disruption to the supply of blood has occurred, specifically at which segment/branch of an artery the vessel is occluded, is important in determining treatment to be administered, whether the ‘route’ to treat the occlusion is unobstructed or stenting is required before treatment, as well as treatment outcome and prognosis. In some instances, a type of treatment used to restore the supply of blood to a region of the brain can depend on the particular location of the cause of the reduction/disruption of blood flow to the tissue. Additionally, the speed at which a diagnosis of presence/absence of an occlusion can be provided and identification of which vessel segment/branch is involved, can also impact the type of treatment, its planning and approach, and the effectiveness of treatment provided to an individual.

In many cases, the tools available to healthcare practitioners to identify blood flow disruptions in the brain are limited. Existing tools are typically unable to provide an array of imaging information that can be helpful to healthcare practitioners in identifying blood flow disruptions. In various scenarios, the views available to healthcare practitioners can include a limited number of brain regions or are only available for a limited number of vessels. Additionally, existing systems are unable to provide curated imaging information to healthcare practitioners in a prompt timeframe that enables accurate and timely diagnoses of conditions stemming from blood flow disruptions in the brain.

Implementations described herein are directed to analyzing imaging data captured of patients to provide images of blood vessels located in the brains and necks of patients to healthcare practitioners to aid the practitioners in identifying abnormalities present in the brains of the patients. The curated images can be generated through the analysis and modification of imaging data produced by one or more imaging technologies. In one or more examples, imaging data generated by one or more computed tomography (CT) imaging techniques, magnetic resonance imaging techniques, and/or digital subtraction imaging techniques can be analyzed and modified to generate a suite of views of blood vessels located in the brains and necks of patients that can be accessed by healthcare practitioners.

In one or more examples, imaging data can be analyzed to determine portions of the imaging data that correspond to a number of anatomical regions. For example, imaging data can be analyzed to separately identify the heads of the patients, the necks of patients, and the aortic arches of patients. The imaging data can also be analyzed to determine arteries present in the different anatomical regions. The imaging data corresponding to the arteries present in the head and neck regions of patients can be modified to enable the rendering of views of the arteries from a number of perspectives. To illustrate, views of vessels in the head and neck of patients can be generated that correspond to the individual brain hemispheres. Additionally, a posterior view and an anterior view of vessels in the head and neck of patients can be rendered based on modified imaging data. Further, imaging data corresponding to arteries in the head and neck regions of patients can be modified to produce three-dimensional views of the arteries. In at least some examples, the three-dimensional views of the arteries can be rotatable.

By analyzing and modifying imaging data obtained from patients according to techniques described herein, a variety of types of images and perspectives for viewing vessels located in the brains and necks of patients can be accessible to healthcare practitioners. In this way, healthcare practitioners can more readily assess the cause and location of blood flow disruptions to the brains of patients. Additionally, functional parameters such as, but not limited to, vessel thickness, degree of stenosis, wall shear stress (to name a few), can be superimposed in color onto a 3D representation of the vessel. As a result, healthcare practitioners can determine effective treatment options and improve outcomes for patients in which a blood flow abnormality or physical or physiological abnormalities are present within, for example, vessels between the aortic arch to the vertex of the brain of a patient.

FIG. 1 is a diagrammatic representation of a computational architecture 100 to analyze imaging data to generate a number of images indicating vessels included in different anatomical regions of the head and neck of patients, according to one or more example implementations. The computational architecture 100 can include an image processing system 102. The image processing system 102 can be implemented by one or more computing devices 104. The one or more computing devices 104 can include one or more server computing devices, one or more desktop computing devices, one or more laptop computing devices, one or more tablet computing devices, one or more mobile computing devices, or combinations thereof. In certain implementations, at least a portion of the one or more computing devices 104 can be implemented in a distributed computing environment. For example, at least a portion of the one or more computing devices 104 can be implemented in a cloud computing architecture. In one or more examples, the one or more computing devices 104 can be part of a cloud computing architecture that provides serverless CPU and GPU computing functionality.

The image processing system 102 can obtain imaging data 106 that is captured with respect to a patient 108. The imaging data 106 can be captured by an imaging data source 110. The imaging data source 110 can include an apparatus that utilizes one or more imaging technologies to generate the imaging data 106. In one or more examples, the imaging data source 110 can implement computed tomography (CT) imaging techniques. In one or more additional examples, the imaging data source 110 can implement magnetic resonance angiography imaging techniques. In still other examples, the imaging data source 110 can implement tomographically reconstructed digital subtraction angiography (DSA) imaging techniques. In one or more illustrative examples, three-dimensional (3D) rotational angiography can be implemented by the imaging data source 110. In one or more additional illustrative examples, the imaging data source 110 can implement C-arm CT imaging techniques.

In various examples, the imaging data 106 can correspond to one or more images of a brain 112 of the patient 108 captured by a CT imaging apparatus. In one or more examples, the CT imaging apparatus can capture a number of images of the brain 112 of the patient 108 over a period of time. In at least some cases, individual images in the series of images can be referred to herein as "slices". The slices can correspond to different regions of the brain 112. For example, a CT imaging apparatus can begin capturing slices of the shoulder or neck of the patient 108 and move up through the base of the skull through the brain 112 and to the top of the head of the patient 108. In one or more examples, the CT imaging apparatus can capture multiple images of a same or similar region of the brain 112 of the patient 108 over time. In various examples, three-dimensional volumes captured by the CT imaging data source 110 can include a number of slices that comprise dynamic phases or temporal frames acquired over a relatively short period of time (e.g., sub-second time frame to less than 5-second time frame). Although the illustrative example of FIG. 1 is described in relation to images of the brain 112 of the patient, the imaging data 106 can correspond to other portions of the patient 108, such as one or more legs of the patient 108, one or more arms of the patient 108, a chest of the patient 108, or an abdomen of the patient 108.

In one or more illustrative examples, a contrast agent can be delivered to the patient 108 and CT images can be captured indicating the flow of the contrast agent through blood vessels that supply blood to the brain 112 of the patient 108. When images are taken while the contrast is still in the arteries, this is called a CT Angiography (CTA). Once the contrast agent drains and images are taken when the contrast agent is in the veins, this is called a CT Venography (CTV). The imaging data 106 can indicate intensity values of voxels of the images captured of the brain 112 of the patient 108. In one or more additional illustrative examples, the imaging data 106 can be generated by a digital subtraction angiography (DSA) imaging apparatus. DSA imaging apparatuses can generate the imaging data 106 by rotating an x-ray source and detector (e.g., flat panel detector) around a patient lying on a table at a relatively slow rate. The x-ray source/flat panel arrangement can rotate less than 360° around the patient, such as about 180°.

The intensity values can be indicated in Hounsfield units (HU). In one or more examples, the intensity values of voxels that correspond to regions of the brain 112 in which the contrast agent is present can be greater than the intensity values of voxels that correspond to regions of the brain 112 in which the contrast agent is not present. In various examples, intensity values of voxels included in the imaging data 106 can indicate an amount of contrast agent present in a region of the brain 112. To illustrate, as the amount of contrast agent present within a region of the brain 112 increases, the intensity values of voxels that correspond to the region can also increase. Further, as the amount of contrast agent present in a region of the brain 112 decreases, the intensity values of voxels that correspond to the region can also decrease.

In still other examples, the imaging data 106 can be generated by a magnetic resonance imaging (MRI) imaging apparatus. For example, magnetic resonance angiography (MRA) imaging techniques can be applied to produce the imaging data 106. In at least some examples, the MRA imaging techniques can be implemented without the use of a contrast agent. To illustrate, the imaging data 106 can be generated using time-of-flight (TOF) MRA imaging techniques. Additionally, phase contrast (PC) MRA imaging techniques can be implemented to generate the imaging data 106. In at least some examples, phase contrast arterial spin labeling (PCASL) MRA imaging techniques can be implemented to generate the imaging data 106. MRA imaging techniques can also be implemented with the use of contrast agent to produce the imaging data 106. In various examples, contrast-enhanced (CE) MRA imaging techniques can be implemented to produce the imaging data 106.

In one or more illustrative examples, the imaging data 106 can be formatted according to a Digital Imaging and Communications in Medicine (DICOM) standard. In addition to data that corresponds to images captured by a CT imaging apparatus, a DSA imaging apparatus, or an MRI imaging apparatus, the imaging data 106 can include additional information about the images captured by the imaging data source 110. For example, the imaging data 106 can include timing data indicating a time at which individual imaging slices of the brain 112 of the patient 108 are captured and/or a time interval at which the individual imaging slices of the brain 112 of the patient 108 are captured, as well as the individual slice position in 3D space relative to a landmark position on the patient (e.g., the nasion). In addition, the imaging data 106 can indicate other characteristics of the imaging slices. To illustrate, the imaging data 106 can indicate at least one of slice thickness, inter-slice distance, voxel dimensions, or voxel locations. The imaging data 106 can also indicate further information, such as at least one of information corresponding to the patient 108, information about the scanning procedure (e.g., kVp, mA, exposure time, helical pitch, reconstruction kernel, type and level of dose reduction algorithm, radiation dose, as well as the type and dose of contrast material), information corresponding to a facility at which the imaging data 106 was generated, or information corresponding to a CT imaging apparatus that captured the images of the brain 112 of the patient 108 included in the imaging data 106.

In at least some examples, the image processing system 102 can include an imaging data preprocessing system 114 to perform one or more preprocessing operations with respect to the imaging data 106. For example, the imaging data preprocessing system 114 can analyze the imaging data 106 with respect to several imaging criteria. To illustrate, the imaging data preprocessing system 114 can analyze the imaging data 106 with respect to one or more field of view criteria. In addition, the imaging data preprocessing system 114 can analyze the imaging data 106 with respect to one or more pixel-related criteria, such as one or more pixel spacing criteria. The imaging data preprocessing system 114 can also analyze the imaging data 106 with respect to one or more slice-related criteria. In one or more illustrative examples, the imaging data preprocessing system 114 can analyze the imaging data 106 with respect to at least one of one or more slice spacing criteria or one or more slice thickness criteria. In still other examples, the imaging data preprocessing system 114 can analyze the imaging data 106 with respect to one or more criteria related to the imaging data source 110, such as one or more peak kilovoltage, reconstruction kernel, or exposure criteria.

In various examples, the imaging data preprocessing system 114 can perform one or more normalization processes with respect to slice distances and/or one or more rescaling processes with respect to Hounsfield Unit values included in the imaging data 106. In one or more additional illustrative examples, the imaging data preprocessing system 114 can perform one or more resampling operations with respect to the imaging data 106. For example, the imaging data preprocessing system 114 can implement one or more filters to resample at least a portion of the imaging data 106. In one or more further illustrative examples, the imaging data preprocessing system 114 can perform a gantry tilt correction process. In one or more examples, a gantry of an imaging apparatus can be tilted during the capture of the imaging data 106. The imaging data preprocessing system 114 can determine whether gantry tilt is present in the imaging data 106 by computationally analyzing the direction of the normal vectors of the slices included in the imaging data 106 and the direction of the vector that connects the slice origins. In situations where the direction of the normal vectors of the slices and the vector that connects the origins of the slices is not collinear, the imaging data preprocessing system 114 can translate the imaging data 106 of each slice relative to a reference slice to correct for gantry tilt. In at least some examples, after performing the one or more preprocessing operations with respect to the imaging data 106, the imaging data preprocessing system 114 can generate modified imaging data 116 that can be available for further processing by other systems and components of the image processing system 102.

The image processing system 102 can include an anatomy detection system 118. The anatomy detection system 118 can analyze the modified imaging data 116 to determine slices of the modified imaging data 116 that correspond to different portions of the anatomy of the head, neck, and chest of the patient 108. In one or more examples, the anatomy detection system 118 can determine first slices of the modified imaging data 116 that correspond to the head of the patient 108. Additionally, the anatomy detection system 118 can determine second slices of the modified imaging data 116 that correspond to the neck of the patient 108. Further, the anatomy detection system 118 can determine third slices of the modified imaging data 116 that correspond to the aortic arch of the patient 108. In various examples, the anatomy detection system 118 can determine additional slices of the modified imaging data 116 that correspond to the carotid arteries of the patient 108.

In at least some examples, the anatomy detection system 118 can generate anatomical identifiers 120 for individual slices of the modified imaging data 116. For example, the anatomy detection system 118 can determine a first identifier for first slices of the modified imaging data 116 corresponding to the head of the patient 108 and determine a second identifier for second slices of the modified imaging data 116 corresponding to the neck of the patient 108. In one or more additional examples, the anatomy detection system 118 can determine a third identifier for third slices of the modified imaging data 116 corresponding to the aortic arch of the patient 108. In still other examples, the anatomy detection system 118 can determine additional identifiers of additional slices of the modified imaging data 116 that correspond to a chest of the patient 108 or an abdomen of the patient 108. In one or more further examples, at least a portion of the anatomical identifiers 120 can indicate one or more slices of the modified imaging data 116 that correspond to one or more anatomical regions with or without contrast agent being present in a given anatomical region.

The image processing system 102 can include a vessel segmentation system 122. The vessel segmentation system 122 can determine portions of the modified imaging data 116 that correspond to vessels included in one or more anatomical regions of the patient 108. In one or more examples, the vessel segmentation system 122 can determine, based on the anatomical identifiers 120, one or more slices of the modified imaging data 116 that correspond to a given anatomical region. The vessel segmentation system 122 can then determine portions of the slices of the modified imaging data 116 that correspond to the vessels of the given anatomical region. In various examples, the vessel segmentation system 122 can determine vessels included in slices of the modified imaging data 116 based on analyzing intensity values of voxels of the slices of the modified imaging data 116. In at least some examples, vessels can be identified from the modified imaging data 116 by determining voxels having intensity differences due to contrast agent, or intensity properties with respect to the local anatomical environment that allow identifying the structure as a vessel based on anatomical location and shape of the structure. In one or more illustrative examples, machine learning based pattern recognition can be used to determine portions of the slices of the modified imaging data 116 that correspond to vessels of the anatomical region.

In the illustrative example of FIG. 1, the vessel segmentation system 122 can determine first slices of the modified imaging data 116 that correspond to a first anatomical region based on a first anatomical identifier included in the anatomical identifiers 120 related to the first slices. The vessel segmentation system 122 can determine first anatomical region vessels 124 included in the first slices corresponding to the first anatomical region. Additionally, the vessel segmentation system 122 can determine second slices of the modified imaging data 116 that correspond to a second anatomical region based on a second anatomical identifier included in the anatomical identifiers 120 related to the second slices. The vessel segmentation system 122 can determine second anatomical region vessels 126 included in the second slices corresponding to the second anatomical region. Further, the vessel segmentation system 122 can determine third slices of the modified imaging data 116 that correspond to a third anatomical region based on a third anatomical identifier included in the anatomical identifiers 120 related to the third slices. The vessel segmentation system 122 can determine third anatomical region vessels 128 included in the third slices corresponding to the third anatomical region. In one or more illustrative examples, the first anatomical region can correspond to a head of the patient, the second anatomical region can correspond to a neck of the patient, and the third anatomical region can correspond to an aortic arch of the patient. Although the illustrative example of FIG. 1 describes the operation of the vessel segmentation system 122 with respect to a first anatomical region, a second anatomical region, and a third anatomical region, the vessel segmentation system 122 can determine vessels of fewer anatomical regions or a greater number of anatomical regions.

In one or more illustrative examples, the vessel segmentation system 122 can execute one or more pattern recognition algorithms to identify slices of the modified imaging data 116 that correspond to various anatomical regions. In at least some examples, the one or more pattern recognition algorithms can include one or more machine learning models that have been trained using training images that have been labeled to indicate one or more anatomical regions. For example, the training images can be labeled to indicate at least one of a head of patients, a neck of patients, an aortic arch of patients, a torso of patients, and the like. In various examples, the one or more machine learning models can be trained to analyze features of the slices that include shape, size, structural combination, intensity values, or one or more combinations thereof to determine slices of the modified imaging data 116 that correspond to one or more anatomical regions. In one or more examples, the one or more machine learning models can analyze features related to bones, muscles, vessels, tendons, one or more combinations thereof, and the like to identify one or more anatomical structures related to one or more slices of the modified imaging data 116. In one or more additional illustrative examples, the vessel segmentation system 122 can execute one or more Deep Q-Network reinforcement machine learning algorithms to move within the image environment to identify slices of the modified imaging data 116 that correspond to one or more anatomical regions. In still other examples, the vessel segmentation system 122 can determine gaussian ball probabilities to identify slices of the modified imaging data 116 that correspond to one or more anatomical regions.

The image processing system 102 can also include an image rendering system 130. The image rendering system 130 can generate a number of output images 132. The image rendering system 130 can generate the output images 132 based on at least a portion of the modified imaging data 116. In various examples, the image rendering system 130 can generate the output images 132 by applying one or more image processing techniques to at least a portion of the modified imaging data 116. In at least some examples, the one or more image processing techniques can be applied to one or more portions of the modified imaging data 116 to generate three-dimensional images and/or rotatable images. The image rendering system 130 can also generate the output images 132 based on the first anatomical region vessels 124, the second anatomical region vessels 126, and the third anatomical region vessels 128.

The output images 132 can be displayed in one or more user interfaces of one or more practitioner computing devices 134 that can be operated by one or more healthcare practitioners 136. The one or more practitioner computing devices 134 can include one or more mobile computing devices, one or more smart phones, one or more tablet computing devices, one or more laptop computing devices, one or more desktop computing devices, one or more medical devices, one or more imaging devices, one or more additional computing devices, or one or more combinations thereof. The one or more practitioner computing devices 134 can be in electronic communication with the image processing system 102. The image processing system 102 can facilitate the communication of various types of information between the one or more practitioner computing devices 134 and the image processing system 102. In various examples, the one or more practitioner computing devices 134 can execute a mobile device application, a browser application, or other image viewing applications or software that can process and display information obtained from the image processing system 102. In one or more illustrative examples, one or more healthcare practitioners 136 can include a doctor, a nurse, a technician, a practitioner assistant, or another healthcare worker that is involved in providing treatment to one or more patients, including the patient 108. Although not shown in the illustrative example of FIG. 1, in one or more additional examples, the patient 108 and/or a representative of the patient 108 can access the output images 132 using one or more further computing devices.

The output images 132 can include anatomical region vessel views 138. The anatomical region vessel views 138 can include at least one of the first anatomical region vessels 124, the second anatomical region vessels 126, or the third anatomical region vessels 128. In one or more examples, the anatomical region vessel views 138 can include one or more groups of vessels included in at least one of the first anatomical region vessels 124, the second anatomical region vessels 126, or the third anatomical region vessels 128. In one or more illustrative examples, the anatomical region vessel views 138 can include a view of vessels of a first hemisphere of the brain 112 of the patient 108 and a view of vessels of a second hemisphere of the brain 112 of the patient 108. The anatomical region vessel views 138 can also include an anterior view of the vessels of the brain 112 of the patient 108 and a posterior view of the vessels of the brain 112 of the patient 108. In one or more additional illustrative examples, the anatomical region vessel views 138 can include solely the anterior circulation that includes both internal carotid arteries, the MCA and the ACA branches, or solely the posterior circulation that includes the vertebral arteries, the basilar artery, SCA, AICA, PICA, and PCA. In at least some examples, the anatomical region vessel views 138 can include the carotid bifurcation or the external carotid artery and middle meningeal artery segments, including potential anastomoses with the ophthalmic artery (e.g., such as anastomosis would be a contraindication for a middle meningeal artery embolization). In still other examples, the anatomical region vessel views 138 can include the visualization of large venous drainage pathways (such as, but not limited to, sagittal and transverse sinus, jugular vein, vein of Galen, as well as large normal and abnormal cortical veins). These large venous drainage pathways can be used to diagnose dural arteriovenous fistula and/or arteriovenous malformations (AVMs).

The output images 132 can also include three-dimensional (3D) vessel views 140. The 3D vessel views 140 can include three-dimensional images of one or more groups of vessels included in the head and/or neck of the patient 108. The 3D vessel views 140 can also include three-dimensional views of one or more individual vessels included in the head and/or neck of the patient 108. In still other examples, the 3D vessel views 140 can include three-dimensional views of one or more segments of one or more vessels included in the head and/or neck of the patient 108. Additionally, the output images 132 can include rotatable vessel views 142. The rotatable vessel views 142 can include views of one or more groups of vessels and/or views of one or more individual vessels included in the neck of the patient, the head of the patient 108, or both the neck and the head of the patient 108. The rotatable vessel views 142 can also include views of one or more segments of one or more vessels included in the neck and/or head of the patient 108. In one or more examples, the rotatable views 142 can include user interfaces that can display images of one or more vessels in the head and/or neck of the patient 108 at different orientations and/or from different points of view.

In one or more examples, the output images 132 can be selected by the one or more healthcare practitioners 136 based on input received from the one or more practitioner computing devices 134. For example, the one or more practitioner computing devices 134 can display one or more user interfaces that include one or more user interface elements that are selectable to indicate at least one of one or more anatomical region vessel views 138, one or more 3D vessel views, or one or more rotatable vessel views 142. In at least some examples, user input with respect to selection of at least one of one or more anatomical region vessel views 138, one or more 3D vessel views, or one or more rotatable vessel views 142 can be obtained in response to actuation of one or more input devices by the one or more healthcare practitioners 136, such as a touch screen, a mouse, a keyboard, a camera, a microphone, a wheel, a joystick, one or more combinations thereof, and the like. In various examples, input related to the output images 132 can also be obtained via one or more graphical user interface elements with respect to modifying magnification of one or more anatomical region vessel views 138, one or more 3D vessel views, one or more rotatable vessel views 142, or one or more combinations thereof. Input devices of the one or more practitioner computing devices 134 can also be used to cause rotation of the rotatable vessel views 142.

Figure 2:
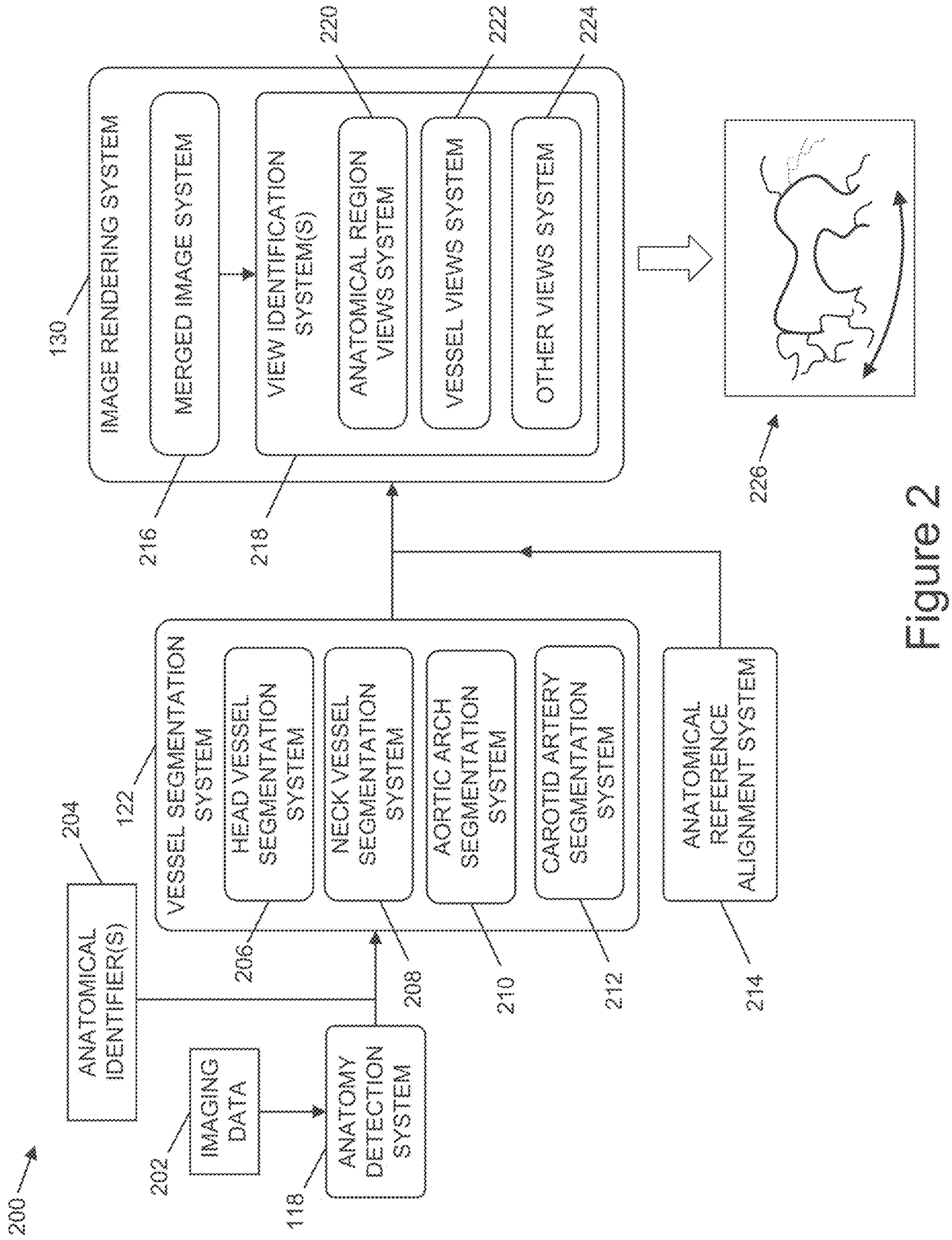
FIG. 2 illustrates a computational framework to analyze imaging data to determine anatomical segments and generate user interfaces including a number of modified images of vessels included in the head and neck of patients, according to one or more implementations.

FIG. 2 illustrates a computational framework 200 to analyze imaging data to determine anatomical segments and generate user interfaces including a number of modified images of vessels included in the head and neck of patients, according to one or more implementations. In various examples, at least a portion of the systems and/or components included in the framework 200 can be included in the image processing system 102 described in relation to FIG. 1. The framework 200 can include the anatomy detection system 118, the vessel segmentation system 122, and the image rendering system 130 described in relation to FIG. 1. In one or more examples, imaging data 202 can be obtained by the anatomy detection system 118. The imaging data 202 can include data obtained from an imaging data source. For example, the imaging data 202 can include CT images obtained from one or more CT imaging devices. In these situations, the imaging data 202 can correspond to the imaging data 106 described in relation to FIG. 1. Additionally, the imaging data 202 can include data generated by one or more imaging data sources that has been preprocessed. In these scenarios, the imaging data 202 can correspond to the modified imaging data 116 described in relation to FIG. 1. In still other examples, the imaging data 202 can include a combination of at least a portion of the imaging data 106 and at least a portion of the modified imaging data 116 described in relation to FIG. 1.

The anatomy detection system 118 can make anatomical identifiers 204 accessible to the vessel segmentation system 122. The anatomical identifiers 204 can correspond to the anatomical identifiers 120 described in relation to FIG. 1. In one or more examples, the anatomical identifiers 204 can include identifiers that indicate slices of the imaging data 202 that correspond to one or more anatomical regions of a patient. In one or more examples, the anatomical identifiers 204 can indicate first slices of the imaging data 202 that correspond to a head region of a patient, second slices of the imaging data 202 that correspond to a neck region of the patient, and third slices of the imaging data 202 that correspond to an aortic arch region of the patient. In at least some examples, the anatomical identifiers 204 can include identifiers of anatomical regions that are not present in the imaging data 202. For example, the anatomical identifiers 204 can include a chest region identifier and an abdomen region identifier. In various examples, slices included in the imaging data 202 may not correspond to a chest region and/or an abdomen region of some patients for which imaging data 202 is generated.

Based on the anatomical identifiers 204, the individual slices of the imaging data 202 can be provided to different machine learning models that comprise the vessel segmentation system 122. The vessel segmentation system 122 can include a head vessel segmentation system 206 that obtains slices of the imaging data 202 that the anatomy detection system 118 determined to be a part of the head region of a patient. Additionally, the vessel segmentation system 122 can include a neck vessel segmentation system 208 that obtains slices of the imaging data 202 that the anatomy detection system 118 determined to be a part of the neck region of the patient. Further, the vessel segmentation system 122 can include an aortic arch segmentation system 210 that the anatomy detection system 118 determined to be a part of the aortic arch of the patient. The vessel segmentation system 122 can also include a carotid artery segmentation system 212 that the anatomy detection system 118 determined to be a part of the carotid artery of the patient. Although the illustrative example of FIG. 2 shows a number of systems included in the vessel segmentation system 122 that perform operations with respect to vessels included in different anatomical regions, in other implementations, the vessel segmentation system 122 can include one or more additional systems that perform segmentation operations with respect to vessels or vessel segments located in other anatomical regions.

The head vessel segmentation system 206 can include a transformer-based machine learning architecture that analyzes first slices of the imaging data 202 that correspond to a head region of the patient to determine voxels of the first slices that correspond to vessels included in the head region of the patient. Additionally, the neck vessel segmentation system 208 can include transformer-based machine learning architectures that analyze second slices of the imaging data 202 that correspond to a neck region of the patient to determine voxels of the second slices that correspond to vessels included in the neck region of the patient. Further, the aortic arch segmentation system 210 can include a transformer-based machine learning architecture that analyzes third slices of the imaging data 202 that correspond to the aortic arch of the patient to determine voxels of the third slices that correspond to vessels included in the aortic arch of the patient. In various examples, the carotid artery segmentation system 212 can include a transformer-based machine learning architecture that analyzes fourth slices of the imaging data 202 that correspond to the carotid artery of the patient to determine voxels of the fourth slices that correspond to vessels included in the carotid artery of the patient.

In at least some examples, the head vessel segmentation system 206, the neck vessel segmentation system 208, the aortic arch segmentation system 210, and/or the carotid artery segmentation system 212 can execute machine learning architectures that are different from transformer-based machine learning architectures. For example, the head vessel segmentation system 206, the neck vessel segmentation system 208, the aortic arch segmentation system 210, and the carotid artery segmentation system 212 can execute machine learning architectures, or one or more combinations thereof, can include one or more convolutional neural networks, one or more residual neural networks, or both. In at least some examples, the head vessel segmentation system 206, the neck vessel segmentation system 208, the aortic arch segmentation system 210, and/or the carotid artery segmentation system 212 can execute machine learning architectures that include a U-Net machine learning framework. In still other examples, the vessel segmentation system 122 can execute one or more machine learning architectures to analyze slices of imaging data corresponding to other vessels or vessel segments located in other anatomical regions.

In one or more illustrative examples, the output from the vessel segmentation system 122 can include a probability map corresponding to the voxels of the individual slices of the imaging data 202 where the probability of an individual voxel included in a vessel is indicated in the probability map.

The framework 200 can also include an anatomical reference alignment system 214. The anatomical reference alignment system 214 can align one or more portions of the segmented imaging data generated by the head vessel segmentation system 206, the neck vessel segmentation system 208, the aortic arch segmentation system 210, and/or the carotid artery segmentation system 212 to an anatomical template. In one or more examples, the anatomical template can indicate anatomical regions of at least one of a human head or neck. In at least some examples, the anatomical template can be generated based on locations of vessels included in imaging data obtained from a number of subjects in which no vessel abnormalities are present. In one or more illustrative examples, the anatomical template can be generated through non-rigid registration and averaging of non-contrast CT imaging data obtained from a number of individuals in which no brain or neck vessel abnormalities were present.

In at least some examples, the anatomical reference alignment system 214 can perform one or more elastic co-registration processes with respect to the anatomical template and the imaging data for the patient generated by the head vessel segmentation system 206, the neck vessel segmentation system 208, the aortic arch segmentation system 210, and the carotid artery segmentation system 212. The one or more elastic co-registration processes can generate rigid transformation and deformation parameters, affine transformation and deformation parameters, non-rigid transformation and deformation parameters, or one or more combinations thereof. The rigid transformation and deformation parameters, the affine transformation and deformation parameters, and/or the non-rigid transformation and deformation parameters can be applied to transform the anatomical template to the data space of the imaging data 202 of the patient. In addition, the rigid, affine, and/or non-rigid transformation and deformation parameters can be used to determine rotational angles of the anatomical template with respect to the data space of the imaging data 202 of the patient. The rotational angles can be used to correct head tilt present with respect to the patient during capture of the imaging data 202.

In various examples, the parameters generated by the anatomical reference alignment system 214 can be used to identify brain tissue and the skull and other bony areas included in the imaging data 202. In this way, voxels corresponding to the skull and other bony areas can be removed from slices included in the imaging data 202. The anatomical reference alignment system 214 can also use the anatomical template information to remove data from the imaging data 202 related to relatively large intracranial veins. For example, the anatomical reference alignment system 214 can remove or otherwise suppress portions of the imaging data 202 related to regions of the sagittal, transverse, and straight venous sinus. Additionally, the anatomical regions generated by the anatomical reference alignment system 214 can be used in conjunction with the anatomical identifiers 204 to determine voxels that are in the anterior regions of the brain of the patient and voxels that are in the posterior regions of the brain of the patient.

In one or more examples, the image rendering system 130 can include a merged image system 216. The merged image system 216 can combine information from the vessel segmentation system 122 and the anatomical reference alignment system 214 to determine voxels corresponding to vessels in the right hemisphere of the brain of the patient and voxels corresponding to vessels in the left hemisphere of the brain of the patient. In various examples, the voxels used to determine vessels in the left hemisphere and the right hemisphere of the brain of the patient can be identified based on one or more contrast agent volume thresholds and intensity value thresholds such that segments having at least a threshold contrast agent volume within an intensity value range can be included to determine vessels included in the left hemisphere and the right hemisphere of the brain of the patient.

In one or more additional examples, the merged image system 216 can perform at least one of one or more maximum intensity projection techniques or one or more volume rendering techniques to generate output images for viewing by one or more healthcare practitioners. In at least some examples, the merged image system 216 can combine the maximum intensity projection images and the volume rendering images with the output from the vessel segmentation system 122 to generate output images that are separated into the head region, the neck region, and the aortic arch region and that remove bony structures and/or calcified plaque present in vessels. In one or more illustrative examples, the vessels included in different regions can be determined by generating a bounding box for the head region and a bounding box for the aortic arch region. The vessels related to the neck region can be those that are between the vessels included in the head region bounding box and the aortic arch region bounding box.

The merged image system 216 can use the probability map generated by the vessel segmentation system and the aligned imaging data with the anatomical template generated by the anatomical reference alignment system 214 to generate a number of images that mask portions of the imaging data 202 corresponding to bony structures, soft tissue, and veins such that arterial vessels are displayed in the images. The merged image system 216 can set the projection plane for the images to rotate along one or more axes. The merged image system 216 can also perform one or more curved planar reformations to generate the output images. The curved planar reformations can be used to generate images of the left and right carotid arteries, the left and right vertebral arteries, and the basilar artery.

In various examples, the merged image system 216 can generate a number of images that are stored in memory of one or more computing devices and accessible using one or more view identification systems 218. The one or more view identification systems 218 can include an anatomical region views system 220. The anatomical region views system 220 can be used to access a first set of images that include vessels located in the head of the patient. The anatomical region views system 220 can also be used to access a second set of images that include vessels located in the neck of the patient. In still other examples, the anatomical region views system 220 can be used to access a third set of images that include the aortic arch of the patient.

The one or more view identification systems 218 can also include a vessel views system 222. The vessel views system 222 can be used to access one or more sets of images that include a single vessel or a single group of vessels. In various examples, the vessel views system 222 can be used to access images that include at least a portion of one or more of the ophthalmic arteries, the left and right vertebral arteries, the basilar artery, the left and right middle cerebral arteries, the anterior communicating artery, the left and right anterior cerebral arteries, the left and right posterior cerebral arteries, the left and right superior cerebellar arteries, the left and right posterior communicating arteries, and the left and right posterior inferior cerebral arteries and the anterior inferior cerebral artery. In one or more additional examples, the vessel views system 222 can also be used to access images that include major veins of the head or neck areas that include at least a portion of one or more jugular veins, one or more transverse sinuses, the vein of Galen, and/or the sagittal sinus. In one or more illustrative examples, at least a portion of the images accessible by the anatomical region views system 220 and the vessel views system 222 can include three-dimensional rotatable images. In various examples, the one or more view identification systems 218 can include an other views system 224 that can be used to access two-dimensional views of vessels included in one or more anatomical regions. An example image 226 generated by the image rendering system 130 is shown in the illustrative example of FIG. 2.

Figure 3:
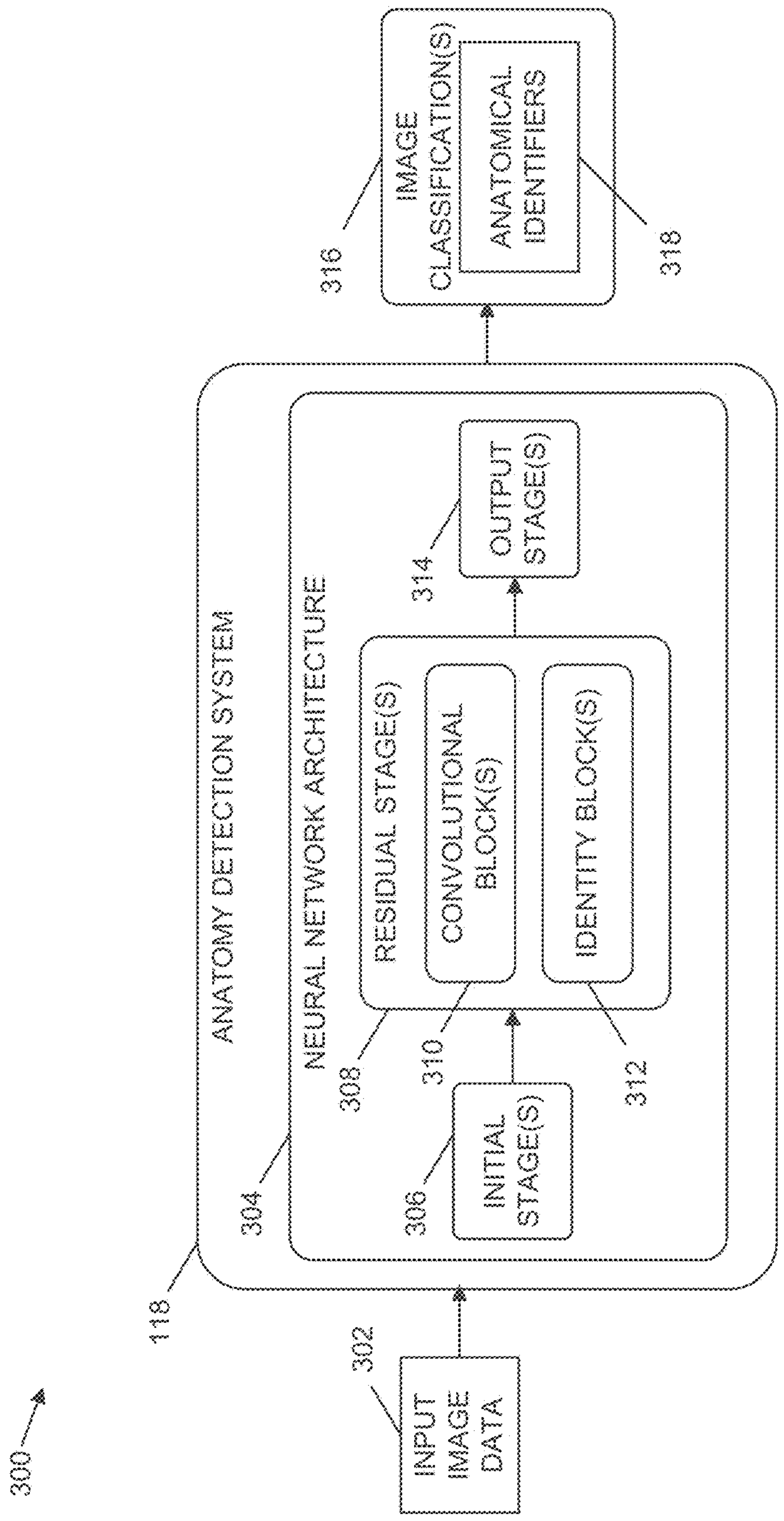
FIG. 3 illustrates a machine learning architecture to analyze imaging data to determine anatomical regions in which blood vessels are present, according to one or more example implementations.

FIG. 3 illustrates a machine learning architecture 300 to analyze imaging data to determine anatomical regions in which blood vessels are present, according to one or more example implementations. The machine learning architecture 300 can include the anatomy detection system 118. The anatomy detection system 118 can obtain input image data 302. The input image data 302 can be image data captured by one or more imaging modalities. In one or more examples, the input image data 302 can include CTA imaging data captured with respect to a patient. In one or more illustrative examples, the input image data 302 can include one or more slices corresponding to at least one of the head or neck of the patient. In one or more examples, the input image data 302 can include slices that are grayscale images. The input image data 302 can include at least one of the imaging data 106 or the modified imaging data 116 described in relation to FIG. 1.

The anatomy detection system 118 can include a neural network architecture 304. The neural network architecture 304 can include one or more initial stages 306. The one or more initial stages 306 can include at least one two-dimensional convolutional layer and a batch normalization layer. Additionally, the one or more initial stages 306 can include a rectifier linear unit (ReLU) activation layer and a max pooling layer. In other examples, the one or more initial stages can include different activation or pooling functions. In one or more illustrative examples, the neural network architecture 304 can include a residual neural network architecture.

Additionally, the neural network architecture 304 can include one or more residual stages 308. Individual residual stages 308 can include one or more convolutional blocks 310 and one or more identity blocks 312. The one or more convolutional blocks 310 included in the individual residual stages 308 can include one or more computational blocks. The one or more computational blocks can include a two-dimensional convolutional layer coupled with a batch normalization layer coupled with an ReLU activation layer, but is not limited to a specific normalization or activation function. The one or more convolutional blocks 310 can include at least one computational block, at least two computational blocks, at least three computational blocks, at least four computational blocks, at least five computational blocks, at least six computational blocks, at least seven computational blocks, or another suitable number of computational blocks. In various examples, the one or more convolutional blocks 310 can include a skip connection that includes a two-dimensional convolutional layer and a batch normalization layer. The skip connection can provide the input of the convolutional block 310 to the output of the convolutional block 310. In various examples, the output of the convolutional block 310 can be joined with the output from the skip connection and fed to, for example, an ReLU layer before being provided to an identity block 312.

In at least one implementation, the one or more identity blocks 312 can include a number of computational blocks comprised of a two-dimensional convolutional layer, a batch normalization layer, and an ReLU layer. The one or more identity blocks 312 can also include a skip connection that does not include a two-dimensional convolutional layer or a batch normalization layer. In various examples, the output from the computational blocks of the identity block can be joined with the input to the identity block via the skip connection and fed to an ReLU layer before being provided to another identity block or to a subsequent convolutional block of an additional residual stage. In one or more illustrative examples, the individual residual stages 308 can include at least one identity block, at least two identity blocks, at least three identity blocks, at least four identity blocks, at least five identity blocks, at least six identity blocks, at least seven identity blocks, at least eight identity blocks, at least nine identity blocks, at least ten identity blocks, or another suitable number of identity blocks. In at least some examples, individual residual stages 308 can include different numbers of identity blocks with respect to one another. In one or more additional illustrative examples, the neural network architecture 304 can include at least one residual stage, at least two residual stages, at least three residual stages, at least four residual stages, at least five residual stages, at least six residual stages, at least seven residual stages, at least eight residual stages, at least nine residual stages, at least ten residual stages, or another suitable number of residual stages.

In one or more examples, the neural network architecture 304 can include one or more output stages 314. The one or more output stages 314 can include at least one two-dimensional average pooling layer. Additionally, the one or more output stages 314 can include a softmax layer or other normalization layer. In at least some examples, the softmax layer can generate probabilities of slices corresponding to one or more image classifications 316. In one or more illustrative examples, the one or more output stages 314 can generate probabilities for slices that correspond to labels including at least one of head with or without contrast material, neck with or without contrast material, chest with or without contrast material, abdomen with or without contrast material, coronary CTA (CCTA) (axial) images, or CTA or NCCT (axial) images that correspond to none of the specified anatomical regions.

In one or more illustrative examples, the number of image classifications 316 can correspond to a number of anatomical classes or identifiers. In at least some examples, the neural network architecture 304 can be trained to analyze the input image data 302 and generate image classifications 316 related to different anatomical regions of the patient for one or more voxels of the input image data 302. For example, the neural network architecture 304 can analyze the input image data 302 to determine voxels included in the input image data 302 that correspond to a head region of a patient. In these situations, the anatomy detection system 118 can generate a first anatomical identifier 318 for the voxels corresponding to the head region. Additionally, the neural network architecture 304 can analyze the input image data 302 to determine voxels included in the input image data 302 that correspond to a neck region of a patient. In these situations, the anatomy detection system 118 can generate a second anatomical identifier 318 for the voxels corresponding to the neck region. Further, the neural network architecture 304 can analyze the input image data 302 to determine voxels included in the input image data 302 that correspond to an aortic arch region of a patient. In these situations, the anatomy detection system 118 can generate a third anatomical identifier 318 for the voxels corresponding to the aortic arch region.

In one or more additional illustrative examples, the anatomy detection system 118 can generate a specified anatomical identifier for a given image slice based on values of the probabilities for the individual classifications determined by the (residual) neural network architecture 304. In various examples, the anatomy detection system 118 can determine an anatomical identifier for individual slices based on determining that a probability for one of the image classifications is greater than a threshold probability, such as at least 50%, at least 55%, at least 60%, at least 65%, at least 70%, at least 75%, or at least 80%, and so forth. In at least some examples, the threshold probability can be determined based on metrics determined for the (residual) neural network architecture 304 related to minimizing an error metric or cost function. In one or more examples, the metrics for evaluating the neural network architecture 304 can include sensitivity, specificity, and/or receiver operating characteristic (ROC) areas under the curve. In one or more additional examples, sensitivity is the ratio of correctly identified positive cases to a total number of positive cases and specificity is the ratio of correctly identified negative cases to a total number of negative cases.

In one or more examples, the neural network architecture 304 can undergo a training process. The training processes can be performed with slices obtained from one or more imaging data sources including non-contrast CT (NCCT) images, CTA images, coronary CTA (CCTA) images, MRA images, DSA CT images, or one or more combinations thereof. The slices can be generated from a number of different manufacturers of imaging data sources. Additionally, the slices can have a number of thicknesses from about 0.1 millimeters (mm) to about 10 mm, from about 0.2 mm to about 8 mm, from about 0.5 mm to about 5 mm, from about 0.5 mm to about 2.5 mm, from about 1 mm to about 3 mm, or from about 2.5 mm to about 5 mm.

In at least some examples, the (residual) neural network architecture 304 can be trained using, but not limited to, a stochastic gradient descent process using an optimizer, such as an Adam optimizer, and a technique to prevent overfitting, such as an L2-or other regularization technique. In one or more illustrative examples, the training process for the (residual) neural network architecture 304 can be performed for a number of epochs, such as at least 10 epochs, at least 25 epochs, at least 50 epochs, at least 75 epochs, at least 100 epochs, or any other number of epochs to achieve the desired convergence. Individual epochs can be trained using a specified batch size and including at least 5000 images per epoch, at least 7500 images per epoch, at least 10,000 images per epoch, at least 12,500 images per epoch, at least 15,000 images per epoch, at least 17,500 images per epoch, at least 20,000 images per epoch, at least 22,500 images per epoch, at least 25,000 images per epoch, or any other number of images per epoch to achieve the desired training results. Additionally, individual epochs can include at least 50 steps, at least 100 steps, at least 150 steps, at least 200 steps, at least 250 steps, at least 300 steps, at least 350 steps, at least 400 steps, or any other number of steps. Further, the slices used in the training process for the (residual) neural network architecture 304 can include labeled images. In one or more illustrative examples, the images can be labeled such that one or more portions of the image are identified with one or more anatomical regions. To illustrate, individual slices included in the training data for the (residual) neural network architecture 304 can include labels corresponding to at least one of head with contrast agent, head without contrast agent, neck with contrast agent, neck without contrast agent, chest with contrast agent, chest without contrast agent, abdomen with contrast agent, abdomen without contrast agent, axial scans generated by CCTA imaging techniques, and so forth.

In various examples, the training images can also be augmented. In one or more examples, the training images can be augmented by performing an offset for intensity values of voxels, such as between −50 Hounsfield Units (HU) to 50 HU, between −40 HU to 40 HU, from −30 HU to 30 HU, from −20 HU to 20 HU, from −10 HU to 10 HU, or any other HU range. In one or more additional examples, the training images can be modified by adding Gaussian noise followed by one or more transformations that can include at least one of rotational transformations or scaling transformations. The rotational transformations can be between −60° and 60°, between −50° and 50°, between −40° and 40°, between −30° and 30°, between −20° and 20°, between −10° and 10°, or any other angular range. The scaling transformations can be at least 80% of the original slice, at least 90% of the original slice, at least 100% of the original slice, at least 110% of the original slice, at least 120% of the original slice, at least 130% of the original slice, at least 140% of the original slice, at least 150% of the original slice, or any other scaling factor.

Figure 4:
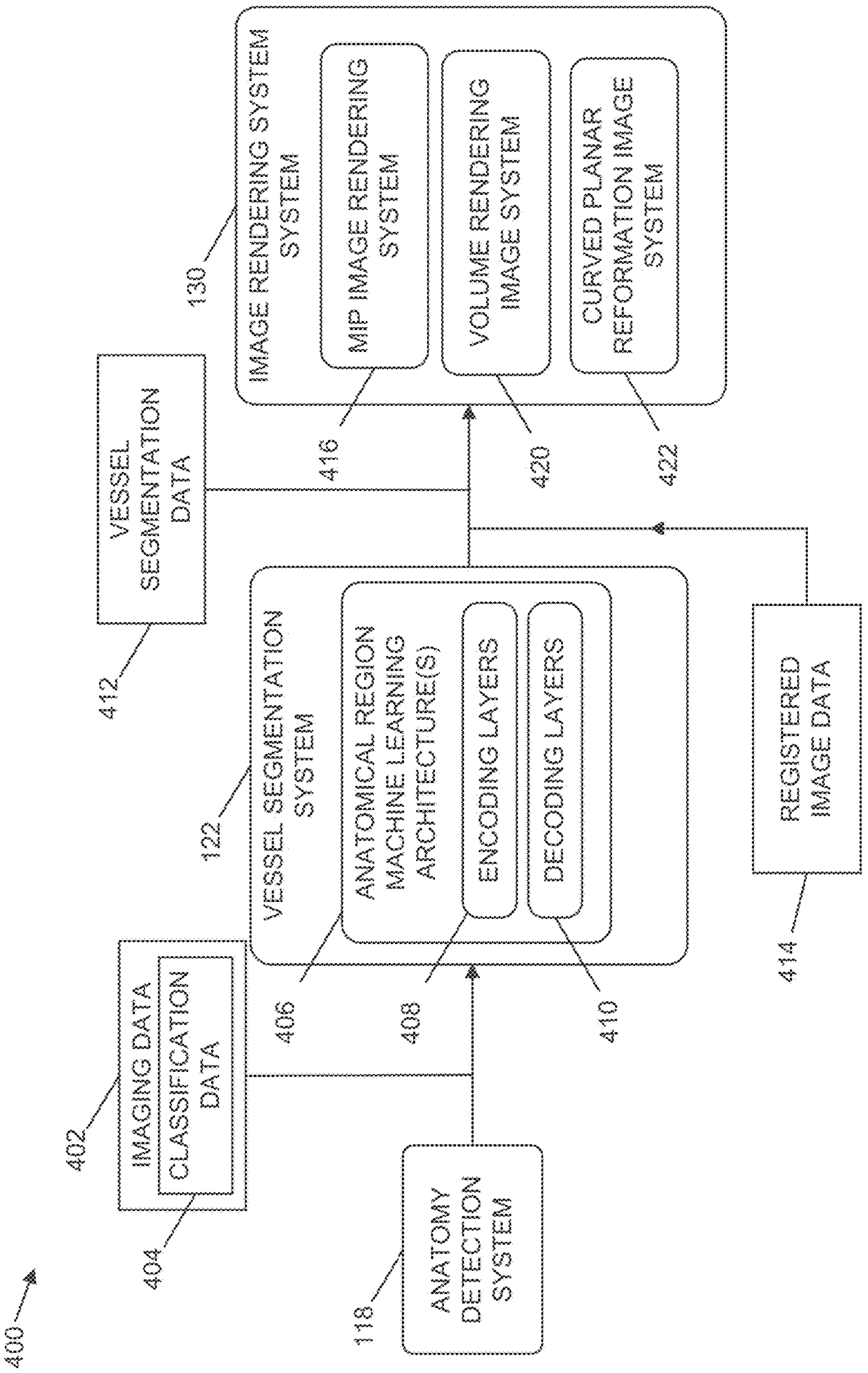
FIG. 4 illustrates a computational architecture to analyze imaging data to generate a number of user interfaces including blood vessels in the head and neck of patients, according to one or more example implementations.

FIG. 4 illustrates a computational architecture 400 to analyze imaging data to generate a number of user interfaces including blood vessels in the head and neck of patients, according to one or more example implementations. The computational architecture 400 can include the anatomy detection system 118 and the vessel segmentation system 122. The anatomy detection system 118 can provide imaging data 402 to the vessel segmentation system 122. The imaging data 402 can include image slices produced by one or more imaging data sources. For example, the imaging data 402 can include at least one of CTA image slices, NCCT image slices, MRA image slices, or tomographically reconstructed DSA image slices. Additionally, the imaging data 402 can include classification data 404 that includes identifiers of slices included in the imaging data 402. In at least some examples, the classification data 404 can include identifiers of anatomical regions determined by the anatomy detection system 118 for individual image slices included in the imaging data 402.

In various examples, the individual anatomical region machine learning architectures 406 can comprise a transformer-based architecture that includes one or more encoding layers 408 and one or more decoding layers 410. In one or more illustrative examples, the vessel segmentation system 122 can include a first anatomical region machine learning architecture to perform segmentation with respect to the head region, a second anatomical region machine learning architecture to perform segmentation with respect to the neck region, and a third anatomical region machine learning architecture to perform segmentation with respect to the aortic arch. In still other examples, the anatomical region machine learning architectures 406 can include a fourth anatomical region machine learning architecture that can perform segmentation corresponding to carotid artery bifurcation.

In one or more additional illustrative examples, at least a portion of the individual anatomical region machine learning architectures 406 can include, but is not limited to, a U-Net machine learning architecture. In at least some examples, the encoding layers 408 of the individual anatomical region machine learning architectures 406 can extract features at multiple resolution levels to determine self-attention mechanism characteristics. The output of the encoding layers 408 can be connected to one or more convolutional neural networks included in the decoding layers 410. In one or more further illustrative examples, at least a portion of the encoding layers 408 and at least a portion of the decoding layers 410 can be connected via a skip connection. In various examples, the anatomical region machine learning architectures 406 can include, but are not limited to, transformer-based machine learning architectures that include blocks comprising a window-based multi-head self-attention layer or a shifted window-based multi-head self-attention layer—where blocks or 2D/3D pixels/voxels are first converted into vectors in conjunction with a multilayer perceptron layer and one or more linear normalization layers.

The anatomical region machine learning architectures 406 can be trained according to one or more training processes. In at least some examples, individual anatomical region machine learning architectures 406 can be trained according to individual training processes. The training data used in the training process for the anatomical region machine learning architectures 406 can include imaging slices generated by at least one of CTA imaging techniques, NCCT imaging techniques, MRA imaging techniques, or tomographically reconstructed DSA imaging techniques. The imaging slices included in the training data can be obtained from training patients having a number of different vessel characteristics. For example, the training data can include image slices obtained from one or more training patients in which at least one of bovine and direct vertebral aortic arch variants, hypoplastic vertebral arteries, or fenestrated arteries are present. Additionally, one or more biological conditions can be present in at least a portion of the training patients. For example, carotid stenosis and/or intracranial aneurysms can be present in at least a portion of the training patients. Additionally, the training patients can include some individuals where no vessel abnormalities are present.

In at least some examples, the training imaging data can include labels directed to segments of vessels in which one or more vessel-related biological conditions can be present. In one or more illustrative examples, the training imaging data can include slices with arteries labeled as at least one of left and right common carotid arteries, at least a portion of the external carotid arteries, left and right internal carotid arteries, at least a portion of the ophthalmic arteries, left and right vertebral arteries (VA), left and right middle cerebral arteries (MCA), the basilar artery (BA), the anterior communicating artery (Acom), at least a portion of the left and right anterior cerebral arteries (ACA), at least a portion of the left and right posterior cerebral arteries (PCA), at least a portion of the left and right superior cerebellar artery (SCA), left and right posterior communicating arteries (Pcom), at least a portion of the left and right posterior inferior cerebellar artery (PICA), at least a portion of the left and right anterior inferior cerebellar artery (AICA), or at least a portion of perforating arteries branching off any of the previously mentioned arteries in this list. In one or more additional illustrative examples, the training imaging data can include slices of veins labeled as one or more superior cerebral veins, one or more inferior cerebral veins, at least a portion of the superficial middle cerebral vein, at least a portion of the superior anastomotic vein, at least a portion of the inferior anastomotic vein, one or more internal cerebral veins, at least a portion of the basal veins of Rosenthal, at least a portion of the basal veins, at least a portion of the great cerebral vein of Galen, one or more superior cerebellar veins, one or more inferior cerebellar veins, one or more dural venous sinuses, or one or more combinations thereof. In one or more further illustrative examples, training data for the aortic arch can be determined through a process that includes atlas registration, image thresholding, morphological operations, and connected component analysis. In still other examples, different portions of the image training data for the aortic arch can be labeled using different methods. For example, a first portion of the training data for the aortic arch can be labeled according to operations comprising bone subtraction, head and neck atlas registration, image thresholding, and connected component analysis. The first portion of the training data can be used to train and generate a machine learning model that can identify the aortic arch segments with carotid and vertebral arteries. A second portion of the training data can be used to refine the machine learning model and the machine learning model can continue to be retrained using additional portions of the image training data.

In still other examples, for generating curved planar reformat images, training data can be produced that indicates left and right carotid artery segmentation into common carotid arteries, external carotid arteries, and internal carotid arteries subsegments. The identification of these segments of the carotid arteries can be used to generate centerlines of the common carotid and internal carotid artery that can be used in generating curved planar reformation images of these arteries. In one or more illustrative examples, the training process for the anatomical region machine learning architectures 406 can also include using a training dataset and a validation dataset for at least one or more portions of the anatomical region machine learning architectures 406. In one or more additional illustrative examples, the training process for the anatomical region machine learning architectures 406 can be performed to minimize the training cost function loss, for example, represented by a Dice coefficient or a cross entropy function. An optimizer, such as an AdamW optimizer, can be used in the training of one or more anatomical region machine learning architectures 406 and the training process can include at least 60 epochs, at least 70 epochs, at least 80 epochs, at least 90 epochs, at least 100 epochs, at least 110 epochs, at least 120 epochs, at least 130 epochs, at least 140 epochs, at least 150 epochs, or any other suitable number of epochs.

The computational architecture 400 can also include the image rendering system 130. The image rendering system 130 can obtain vessel segmentation data 412 from the vessel segmentation system 122. The vessel segmentation data 412 can include slices of imaging data that correspond to individual anatomical regions. In one or more examples, the vessel segmentation data 412 can include slices corresponding to head regions of patients. In one or more additional examples, the vessel segmentation data 412 can include slices corresponding to neck regions of patients. In one or more further examples, the vessel segmentation data 412 can include slices corresponding to aortic arches of patients. In still other examples, the vessel segmentation data 412 can include slices corresponding to carotid arteries of patients.

Registered image data 414 can also be accessed by the image rendering system 130. The registered image data 414 can include at least a portion of the slices included in the vessel segmentation data 412 that are registered with one or more anatomical templates. In various examples, the registered image data 414 can include images for which bone and tissue features of images have been removed. In at least some examples, the image rendering system 130 can determine slices included in at least one of the vessel segmentation data 412 or the registered image data 414 satisfying one or more image quality criteria before being used to generate images viewable by healthcare practitioners. The one or more image quality criteria can correspond to the statistical distribution and/or spatial structural ordering of the voxel values included in the slices. In one or more illustrative examples, the one or more image quality criteria can correspond to a minimum number of Hounsfield units (HU) of voxels, such as at least 10 HU, at least 20 HU, at least 30 HU, at least 40 HU, at least 50 HU, at least 60 HU, at least 70 HU, at least 80 HU, at least 90 HU, at least 100 HU, or any other minimum HU number. In one or more additional illustrative examples, the one or more image quality criteria can correspond to a minimum amount of contrast agent present in vessels present in slices of at least one of the vessel segmentation data 412 or the registered image data 414.

In one or more further illustrative examples, the image rendering system 130 can determine metal artifacts or other objects that can be present in head and/or neck regions of patients. In at least some examples, the image rendering system 130 can determine metal artifacts and other objects present in head and/or neck regions of patients by applying one or more additional criteria. The one or more additional criteria can include brightness measurements of at least 800 HU, at least 850 HU, at least 900 HU, at least 950 HU, at least 1000 HU, at least 1050 HU, at least 1100 HU, at least 1150 HU, at least 1200 HU, at least 1250 HU, or any other HU brightness criteria. The one or more additional criteria can also include volume related criteria, such as at least 0.01 centimeters$^3$ ($cm^3$), at least 0.03 $cm^3$, at least 0.05 $cm^3$, at least 0.08 $cm^3$, at least 0.10 $cm^3$, at least 0.12 $cm^3$, at least 0.15 $cm^3$, at least 0.18 $cm^3$, at least 0.20 $cm^3$, at least 0.25 $cm^3$, or any other volume related criteria. In various examples, the image rendering system 130 can remove metal and/or metal-induced imaging/reconstruction artifacts from imaging data of patients.

The image rendering system 130 can generate a plurality of images that are viewable by healthcare practitioners based on the vessel segmentation data 412 and the registered image data 414. The image rendering system 130 can include a maximum intensity projection (MIP) image rendering system 416. The MIP image rendering system 416 can implement one or more ray tracing techniques to produce MIP images of relatively large vessels. In at least some examples, the MIP image rendering system 416 can produce MIP images that are rotatable around at least one of the x-axis, the y-axis, the z-axis, or any other axis in 3D space. The MIP images generated by the MIP image rendering system 416 can include MIP images of vessels located in, but not limited to, head regions of patients. In at least some examples, the MIP image rendering system 416 can generate MIP images corresponding to at least one of a posterior view of vessels included in the head region of patients, an anterior view of vessels included in the head region of patients, a left hemisphere view of vessels included in the head region of patients, or a right hemisphere view of vessels included in the head region of patients. The MIP image rendering system 416 can also generate MIP images corresponding to vessels located in the neck region of patients. In still other examples, the MIP image rendering system 416 can generate MIP images corresponding to the aortic arch of patients.

The image rendering system 130 can also include a volume rendering image system 420. The volume rendering image system 420 can generate volume rendered images by implementing direct volume rendering techniques with respect to at least one of the vessel segmentation data 412 or the registered image data 414. The direct volume rendering techniques can include performing ray casting in conjunction with executing one or more transfer functions to assign colors and gradients to voxels along the ray. The volume rendering image system 420 can generate volume rendered images of at least one of head regions or neck regions of patients that are rotatable along at least one of the x-axis, the y-axis, the z-axis, or any axis in 3D space.

In addition, the image rendering system 130 can include a curved planar reformation image system 422. The curved planar reformation image system 422 can generate curved planar reformation images of at least one of the vessels or at least one of the vessel segments supplying blood to the brains of patients. In one or more examples, the curved planar reformation image system 422 can generate curved planar reformation images of at least one of the right carotid artery, the left carotid artery, the right vertebral artery, or the left vertebral artery of the brains of patients. In one or more examples, the curved planar reformation image system 422 can generate two-dimensional images that can be elongated and otherwise modified based on user input to aid in identifying vessel related conditions, such as stenosis, occlusions, aneurysms, and the like. In at least some examples, the curved planar reformation image system 422 can generate curved planar reformation images by determining a centerline of a given vessel. The centerline of vessels can be determined by generating a surface representation of the aortic arch, the carotid arteries, the vertebral arteries, and/or the basilar artery based on the vessel segmentation data 412. In various examples, the centerline of vessels can be determined by identifying one or more landmarks of the vessels. The one or more landmarks can include a proximal point of reference and a distal point of reference. In at least some examples, the curved planar reformation image system 422 can determine a shortest path between endpoints of a vessel segment. In one or more illustrative examples, the centerline of a vessel can be represented as coordinates of a set of connected points included in a vessel segment between two branching points.

Figure 5:
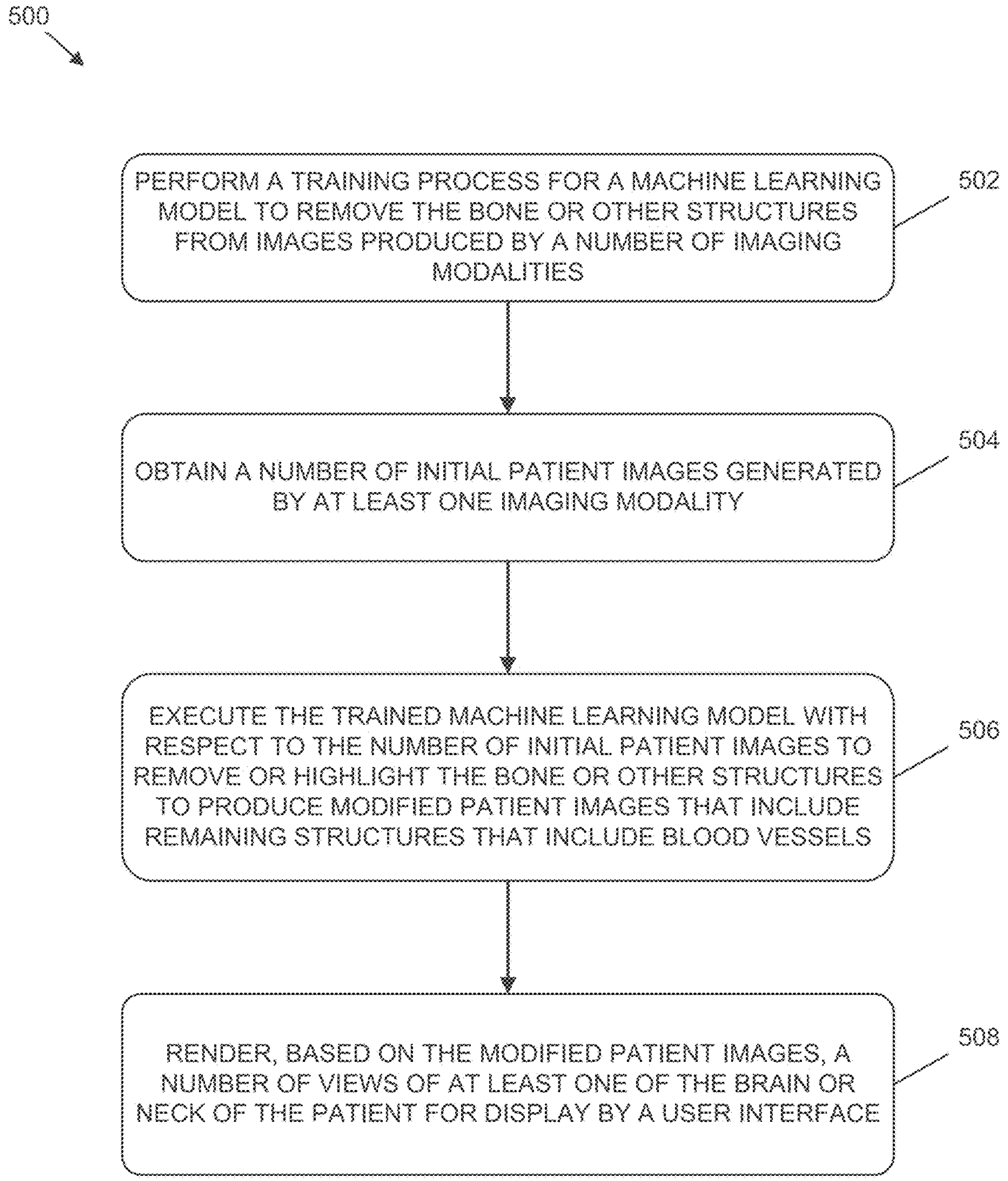
FIG. 5 is a flow diagram of a process to analyze imaging data to generate a number of user interfaces including blood vessels in the head and neck of patients, according to one or more example implementations.

FIG. 5 is a flow diagram of a process 500 to analyze imaging data to generate a number of user interfaces including blood vessels in the head and neck of patients, according to one or more example implementations. The process 500 can include, at 502, performing a training process for a machine learning model to remove the bone or other anatomical structures from images produced by a number of imaging modalities. In at least some examples, the other anatomical structures can include at least one of tissue, blood vessels, or plaque. In one or more examples, one or more anatomical structures, such as blood vessels, can remain after the bone or other anatomical structures are removed or otherwise highlighted by the machine learning model.

At 504, the process 500 can include obtaining a number of initial patient images generated by at least one imaging modality. In one or more examples, the at least one imaging modality can include at least one of computed tomography angiography (CTA), magnetic resonance angiography (MRA), or tomographically-reconstructed digital subtraction angiography (DSA).

At 506, the process 500 can include executing the trained machine learning model with respect to the number of initial patient images to remove or highlight the bone or other structures to produce modified patient images that include remaining structures that include blood vessels. In one or more examples, the trained machine learning model can include a first machine learning architecture that can analyze the number of initial images to determine a first portion of the number of initial images corresponding to a first anatomical region of the patient and a second portion of the number of initial images corresponding to a second anatomical region of the patient, the first anatomical region and the second anatomical region corresponding to at least two of the head region, the neck region, or the aortic arch. In one or more illustrative examples, the first machine learning architecture can include a residual neural network architecture. Additionally, the first machine learning architecture can output a probability map indicating one or more probabilities of individual initial images corresponding to at least one of the first anatomical region or the second anatomical region. In various examples, the trained machine learning model can also include a second machine learning architecture that can analyze, based on the probability map, the number of initial images to determine segmentation data for blood vessels included in the first anatomical region and the second anatomical region. In at least some examples, the second machine learning architecture can include at least one (transformer-based) machine learning architecture.

At 508, the process 500 can include rendering, based on the modified patient images, a number of views of at least one of the brain or neck of the patient for display by a user interface. In one or more examples, the number of views can include predetermined views of one or more blood vessel segments. In addition, the predetermined views can be accessible in response to input from a user of the one or more computing devices selecting one or more user interface elements corresponding to predetermined views. In various examples, the predetermined views include at least one of one or more maximum intensity projection views, one or more volume rendered views, or one or more curved planar reformation views. In at least some examples, the one or more curved planar reformation views can be generated by determining a centerline of at least one blood vessel included in the one or more curved planar reformation views.

In one or more illustrative examples, the predetermined views can include the Circle of Willis viewed from a plurality of perspectives, one or more segments of the left carotid artery viewed from a plurality of perspectives, one or more segments of the right carotid artery viewed from a plurality of perspectives, one or more segments of the (left/right) middle cerebral artery viewed from a plurality of perspectives, one or more segments of the (left/right) internal carotid artery viewed from a plurality of perspectives, one or more segments of the (left/right) anterior cerebral artery viewed from a plurality of perspectives, one or more segments of the (left/right) posterior cerebral artery viewed from a plurality of perspectives, one or more segments of the (left/right) vertebral artery viewed from a plurality of perspectives, one or more segments of the basilar artery viewed from a plurality of perspectives, one or more segments of one or more superior cerebral veins viewed from a plurality of perspectives, one or more segments of one or more inferior cerebral veins viewed from a plurality of perspectives, one or more segments of the superficial middle cerebral vein viewed from a plurality of perspectives, one or more segments of the superior anastomotic vein viewed from a plurality of perspectives, one or more segments of the inferior anastomotic vein viewed from a plurality of perspectives, one or more segments of one or more internal cerebral veins viewed from a plurality of perspectives, one or more segments of the basal veins of Rosenthal viewed from a plurality of perspectives, one or more segments of the basal veins, at least a portion of the great cerebral vein of Galen viewed from a plurality of perspectives, one or more segments of one or more superior cerebellar veins viewed from a plurality of perspectives, one or more segments of one or more inferior cerebellar veins viewed from a plurality of perspectives, one or more segments of one or more dural venous sinuses viewed from a plurality of perspectives, or one or more combinations thereof.

In one or more additional illustrative examples, additional input can be received to cause at least a portion of the remaining anatomical structures included in the number of modified patient images to be removed. For example, based on the additional input, one or more additional modified patient images can be generated that reduce the number of blood vessels being viewed by a user. In at least some examples, the one or more additional modified patient images can include at least one of a first view of first blood vessels included in a left hemisphere of the brain of the patient, a second view of second blood vessels included in a right hemisphere of the brain of the patient, a third view of third blood vessels included in an anterior region of the brain of the patient, and a fourth view of fourth blood vessels included in a posterior region of the brain of the patient.

In one or more further illustrative examples, the number of views of at least one of the head region or the neck region of the patient can be modified to indicate one or more vessel characteristics that can include at least one of blood flow patterns, vessel curvature, vessel diameters, blood vessel wall shear stress, plaque, plaque density, plaque type located in one or more vessels, or stenosis grading. Additionally, values related to measurements of the one or more vessel characteristics can be displayed as one or more overlays in the number of views according to one or more color schemes, one or more brightness schemes, or one or more shading schemes. For example, (pseudo) color code can be overlaid on vessel features in images that is representative of quantitative parameters, such as at least one of blood flow patterns, vessel curvature, vessel diameters, blood vessel wall shear stress, plaque, plaque density, plaque type located in one or more vessels, or stenosis grading.

In still other examples, the number of views can be used to determine a treatment plan for the patient with respect to a vessel abnormality. In one or more examples, the number of views can indicate one or more anatomical landmarks that can be used in determining the treatment plan for the patient. In addition, the number of views and an additional number of views for the patient can be determined over a period of time. In various examples, based on the additional number of views, at least one of an amount of progression of a blood vessel-related biological condition, a response to treatment for the blood vessel-related biological condition, a relapse of the blood vessel-related biological condition, or guidance for treatment of the blood vessel-related biological condition can be determined. Further, the number of views and the additional number of views of the patient can be combined to generate one or more aggregate views that indicate changes to one or more vessel characteristics of the patient over the period of time, the one or more vessel characteristics including at least one of blood flow patterns, vessel curvature, vessel diameters, blood vessel wall shear stress, plaque, plaque type located in one or more vessels, or stenosis grading.

Figure 6:
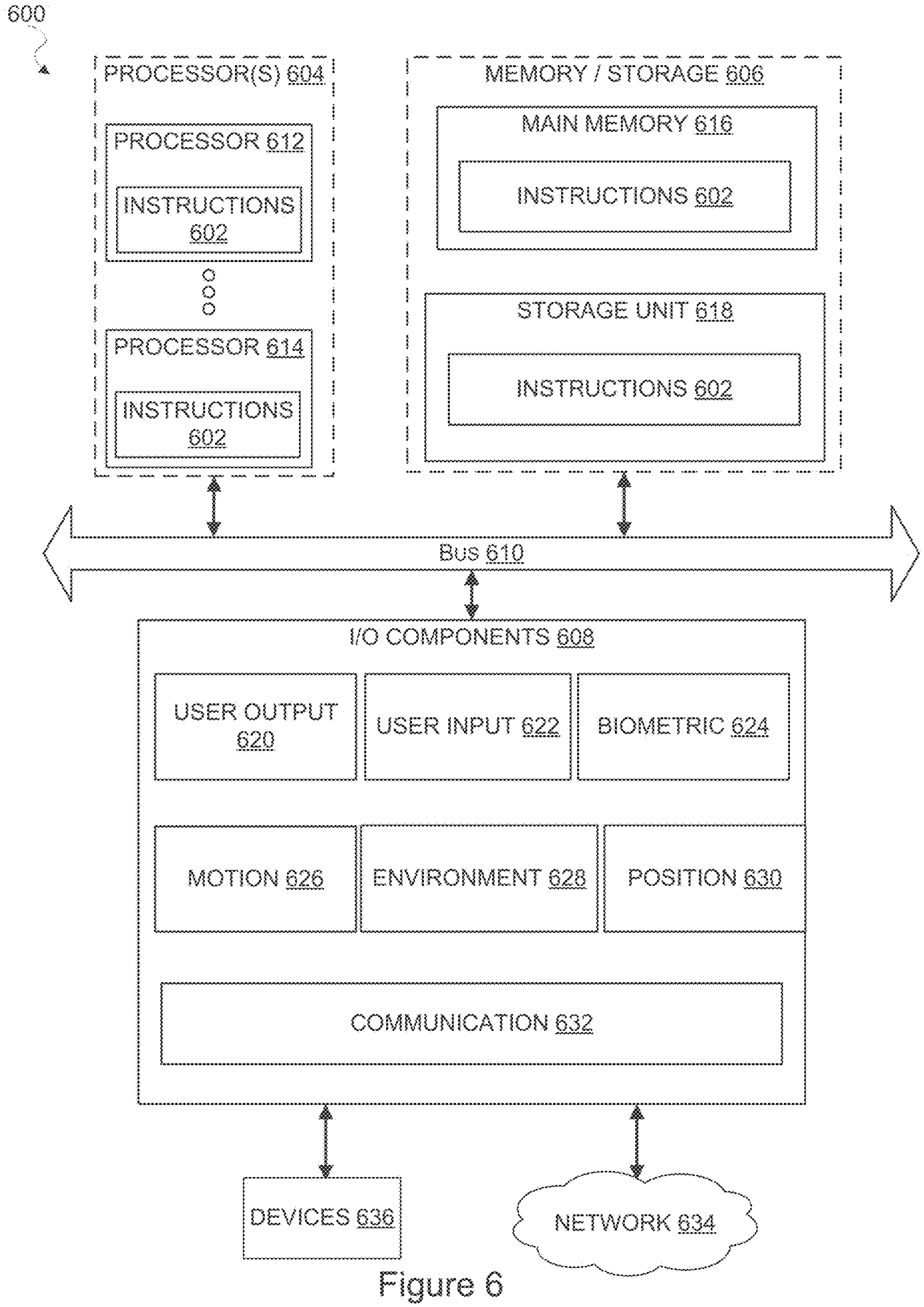
FIG. 6 is a block diagram illustrating components of a machine, in the form of a computer system, that may read and execute instructions from one or more machine-readable media to perform any one or more methodologies described herein, in accordance with one or more example implementations.

FIG. 6 is a block diagram illustrating components of a machine 600, according to some example implementations, able to read instructions from a machine-readable medium (e.g., a machine-readable storage medium) and perform any one or more of the methodologies discussed herein. Specifically, FIG. 6 shows a diagrammatic representation of the machine 600 in the example form of a computer system, within which instructions 602 (e.g., software, a program, an application, an applet, an app, or other executable code) for causing the machine 600 to perform any one or more of the methodologies discussed herein may be executed. As such, the instructions 602 may be used to implement modules or components described herein. The instructions 602 transform the general, non-programmed machine 600 into a particular machine 600 programmed to carry out the described and illustrated functions in the manner described. In alternative implementations, the machine 600 operates as a standalone device or may be coupled (e.g., networked) to other machines. In a networked deployment, the machine 600 may operate in the capacity of a server machine or a client machine in a server-client network environment, or as a peer machine in a peer-to-peer (or distributed) network environment. The machine 600 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, at network switch, a network bridge, or any machine capable of executing the instructions 602, sequentially or otherwise, that specify actions to be taken by machine 600. Further, while only a single machine 600 is illustrated, the term "machine" shall also be taken to include a collection of machines that individually or jointly execute the instructions 602 to perform any one or more of the methodologies discussed herein.

The machine 600 may include processors 604, memory/storage 606, and I/O components 608, which may be configured to communicate with each other such as via a bus 610. "Processor" in this context, refers to any circuit or virtual circuit (a physical circuit emulated by logic executing on an actual processor 604) that manipulates data values according to control signals (e.g., "commands," "op codes," "machine code," etc.) and which produces corresponding output signals that are applied to operate a machine 600. In an example implementation, the processors 604 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 612 and a processor 614 that may execute the instructions 602. The term "processor" is intended to include multi-core processors 604 that may comprise two or more independent processors (sometimes referred to as "cores") that may execute instructions 602 contemporaneously. Although FIG. 6 shows multiple processors 604, the machine 600 may include a single processor 612 with a single core, a single processor 612 with multiple cores (e.g., a multi-core processor), multiple processors 612, 614 with a single core, multiple processors 612, 614 with multiple cores, or any combination thereof.

The memory/storage 606 may include memory, such as a main memory 616, or other memory storage, and a storage unit 618, both accessible to the processors 604 such as via the bus 610. The storage unit 618 and main memory 616 store the instructions 602 embodying any one or more of the methodologies or functions described herein. The instructions 602 may also reside, completely or partially, within the main memory 616, within the storage unit 618, within at least one of the processors 604 (e.g., within the processor's cache memory), or any suitable combination thereof, during execution thereof by the machine 600. Accordingly, the main memory 616, the storage unit 618, and the memory of processors 604 are examples of machine-readable media. "Machine-readable media," also referred to herein as "computer-readable storage media", in this context, refers to a component, device, or other tangible media able to store instructions 602 and data temporarily or permanently and may include, but is not limited to, random-access memory (RAM), read-only memory (ROM), buffer memory, flash memory, optical media, magnetic media, cache memory, other types of storage (e.g., erasable programmable read-only memory (EEPROM)) and/or any suitable combination thereof. The term "machine-readable medium" may be taken to include a single medium or multiple media (e.g., a centralized or distributed database, or associated caches and servers) able to store instructions 602. The term "machine-readable medium" shall also be taken to include any medium, or combination of multiple media, that is capable of storing instructions 602 (e.g., code) for execution by a machine 600, such that the instructions 602, when executed by one or more processors 604 of the machine 600, cause the machine 600 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 608 may include a wide variety of components to receive input, provide output, produce output, transmit information, exchange information, capture measurements, and so on. The specific I/O components 608 that are included in a particular machine 600 will depend on the type of machine. For example, portable machines such as mobile phones will likely include a touch input device or other such input mechanisms, while a headless server machine will likely not include such a touch input device. It will be appreciated that the I/O components 608 may include many other components that are not shown in FIG. 6. The I/O components 608 are grouped according to functionality merely for simplifying the following discussion and the grouping is in no way limiting. In various example implementations, the I/O components 608 may include user output components 620 and user input components 622. The user output components 620 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 622 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location or force of touches or touch gestures, or other tactile input components), audio input components (e.g., a microphone), and the like.

In further example implementations, the I/O components 608 may include biometric components 624, motion components 626, environmental components 628, or position components 630 among a wide array of other components. For example, the biometric components 624 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 626 may include acceleration sensor components (e.g., accelerometer), gravitation sensor components, rotation sensor components (e.g., gyroscope), and so forth. The environmental components 628 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 630 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 608 may include communication components 632 operable to couple the machine 600 to a network 634 or devices 636. For example, the communication components 632 may include a network interface component or other suitable device to interface with the network 634. In further examples, communication components 632 may include wired communication components, wireless communication components, cellular communication components, near field communication (NFC) components, Bluetooth® components (e.g., Bluetooth® Low Energy), Wi-Fi® components, and other communication components to provide communication via other modalities. The devices 636 may be another machine 600 or any of a wide variety of peripheral devices (e.g., a peripheral device coupled via a USB).

Moreover, the communication components 632 may detect identifiers or include components operable to detect identifiers. For example, the communication components 632 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 632, such as location via Internet Protocol (IP) geo-location, location via Wi-Fi® signal triangulation, location via detecting an NFC beacon signal that may indicate a particular location, and so forth.

"Component," in this context, refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example implementations, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application-specific integrated circuit (ASIC). A hardware component may also include programmable logic or circuitry that is temporarily configured by software to perform certain operations. For example, a hardware component may include software executed by a general-purpose processor 604 or other programmable processor. Once configured by such software, hardware components become specific machines (or specific components of a machine 600) uniquely tailored to perform the configured functions and are no longer general-purpose processors 604. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering implementations in which hardware components are temporarily configured (e.g., programmed), each of the hardware components need not be configured or instantiated at any one instance in time. For example, where a hardware component comprises a general-purpose processor 604 configured by software to become a special-purpose processor, the general-purpose processor 604 may be configured as respectively different special-purpose processors (e.g., comprising different hardware components) at different times. Software accordingly configures a particular processor 612, 614 or processors 604, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In implementations in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices, and can operate on a resource (e.g., a collection of information). The various operations of example methods described herein may be performed, at least partially, by one or more processors 604 that are temporarily configured (e.g., by software) or permanently configured to perform the relevant operations. Whether temporarily or permanently configured, such processors 604 may constitute processor-implemented components that operate to perform one or more operations or functions described herein. As used herein, "processor-implemented component" refers to a hardware component implemented using one or more processors 604. Similarly, the methods described herein may be at least partially processor-implemented, with a particular processor 612, 614 or processors 604 being an example of hardware. For example, at least some of the operations of a method may be performed by one or more processors 604 or processor-implemented components. Moreover, the one or more processors 604 may also operate to support performance of the relevant operations in a "cloud computing" environment or as a "software as a service" (SaaS). For example, at least some of the operations may be performed by a group of computers (as examples of machines 600 including processors 604), with these operations being accessible via a network 634 (e.g., the Internet) and via one or more appropriate interfaces (e.g., an API). The performance of certain of the operations may be distributed among the processors, not only residing within a single machine 600, but deployed across a number of machines. In some example implementations, the processors 604 or processor-implemented components may be located in a single geographic location (e.g., within a home environment, an office environment, or a server farm). In other example implementations, the processors 604 or processor-implemented components may be distributed across a number of geographic locations.

Figure 7:
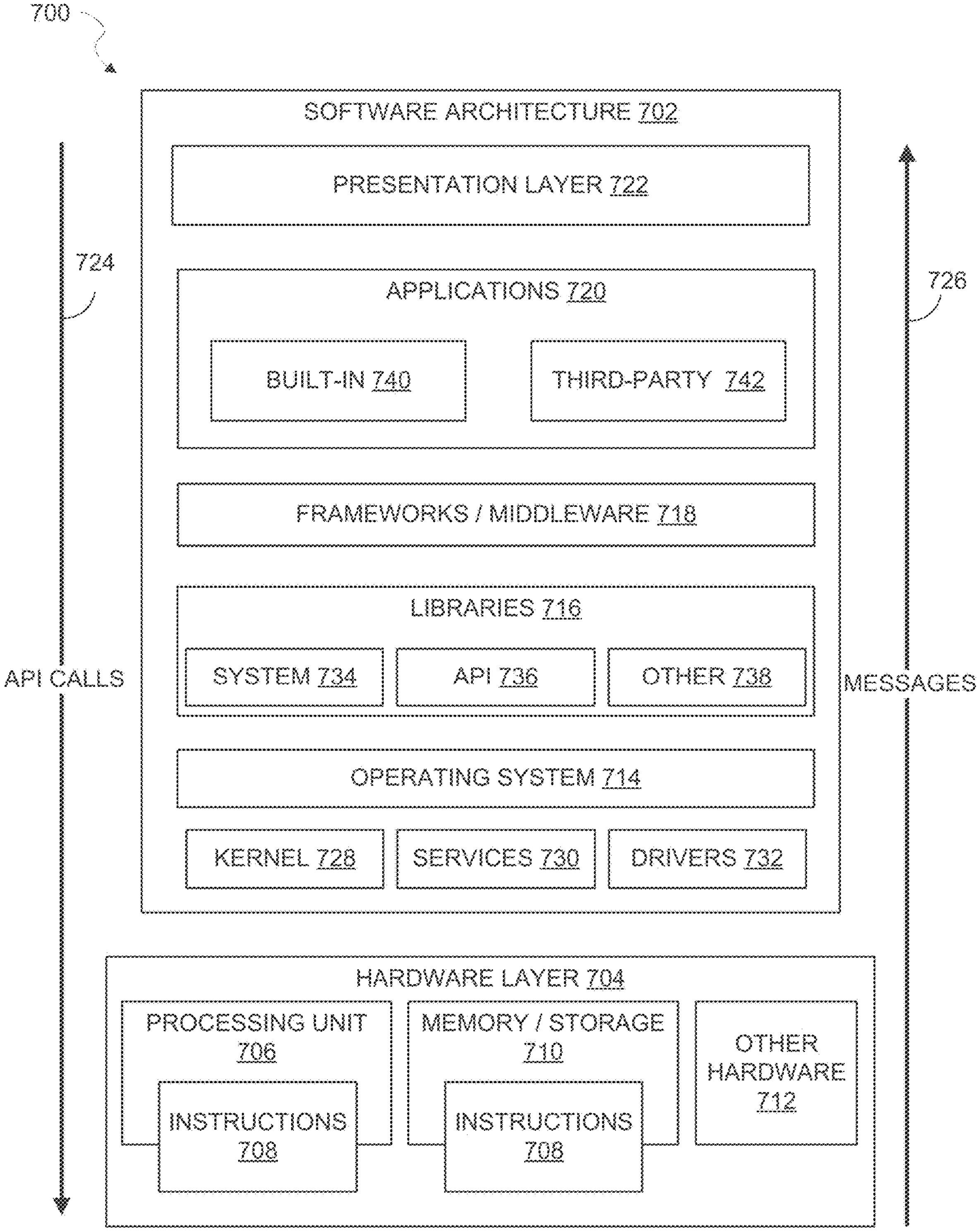
FIG. 7 is a block diagram illustrating a representative software architecture that may be used in conjunction with one or more hardware architectures described herein, in accordance with one or more example implementations.

FIG. 7 is a block diagram illustrating system 700 that includes an example software architecture 702, which may be used in conjunction with various hardware architectures herein described. FIG. 7 is a non-limiting example of a software architecture and it will be appreciated that many other architectures may be implemented to facilitate the functionality described herein. The software architecture 702 may execute on hardware such as machine 600 of FIG. 6 that includes, among other things, processors 604, memory/storage 606, and input/output (I/O) components 608. A representative hardware layer 704 is illustrated and can represent, for example, the machine 600 of FIG. 6. The representative hardware layer 704 includes a processing unit 706 having associated executable instructions 708. Executable instructions 708 represent the executable instructions of the software architecture 702, including implementation of the methods, components, and so forth described herein. The hardware layer 704 also includes at least one of memory or storage modules memory/storage 710, which also have executable instructions 708. The hardware layer 704 may also comprise other hardware 712.

In the example architecture of FIG. 7, the software architecture 702 may be conceptualized as a stack of layers where each layer provides particular functionality. For example, the software architecture 702 may include layers such as an operating system 714, libraries 716, frameworks/middleware 718, applications 720, and a presentation layer 722. Operationally, the applications 720 or other components within the layers may invoke API calls 724 through the software stack and receive messages 726 in response to the API calls 724. The layers illustrated are representative in nature and not all software architectures have all layers. For example, some mobile or special purpose operating systems may not provide a frameworks/middleware 718, while others may provide such a layer. Other software architectures may include additional or different layers.

The operating system 714 may manage hardware resources and provide common services. The operating system 714 may include, for example, a kernel 728, services 730, and drivers 732. The kernel 728 may act as an abstraction layer between the hardware and the other software layers. For example, the kernel 728 may be responsible for memory management, processor management (e.g., scheduling), component management, networking, security settings, and so on. The services 730 may provide other common services for the other software layers. The drivers 732 are responsible for controlling or interfacing with the underlying hardware. For instance, the drivers 732 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 716 provide a common infrastructure that is used by at least one of the applications 720, other components, or layers. The libraries 716 provide functionality that allows other software components to perform tasks in an easier fashion than to interface directly with the underlying operating system 714 functionality (e.g., kernel 728, services 730, drivers 732). The libraries 716 may include system libraries 734 (e.g., C standard library) that may provide functions such as memory allocation functions, string manipulation functions, mathematical functions, and the like. In addition, the libraries 716 may include API libraries 736 such as media libraries (e.g., libraries to support presentation and manipulation of various media formats, such as MPEG4, H.264, MP3, AAC, AMR, JPG, PNG), graphics libraries (e.g., an OpenGL framework that may be used to render two-dimensional and three-dimensional graphic content on a display), database libraries (e.g., SQLite that may provide various relational database functions), web libraries (e.g., WebKit that may provide web browsing functionality), and the like. The libraries 716 may also include a wide variety of other libraries 738 to provide many other APIs to the applications 720 and other software components/modules.

The frameworks/middleware 718 (also sometimes referred to as middleware) provide a higher-level common infrastructure that may be used by the applications 720 or other software components/modules. For example, the frameworks/middleware 718 may provide various graphical user interface functions, high-level resource management, high-level location services, and so forth. The frameworks/middleware 718 may provide a broad spectrum of other APIs that may be utilized by the applications 720 or other software components/modules, some of which may be specific to a particular operating system 714 or platform.

The applications 720 include built-in applications 740 and third-party applications 742. Examples of representative built-in applications 740 may include, but are not limited to, a contacts application, a browser application, a book reader application, a location application, a media application, a messaging application, or a game application. Third-party applications 742 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 742 may invoke the API calls 724 provided by the mobile operating system (such as operating system 714) to facilitate functionality described herein.

The applications 720 may use built-in operating system functions (e.g., kernel 728, services 730, drivers 732), libraries 716, and frameworks/middleware 718 to create UIs to interact with users of the system. Alternatively, or additionally, in some systems, interactions with a user may occur through a presentation layer, such as presentation layer 722. In these systems, the application/component "logic" can be separated from the aspects of the application/component that interact with a user.

Changes and modifications may be made to the disclosed implementations without departing from the scope of the present disclosure. These and other changes or modifications are intended to be included within the scope of the present disclosure, as expressed in the following claims.

What is claimed is:

1. A method comprising:

performing a training process for a machine learning model using training data that includes a number of training images, wherein a plurality of anatomical structures are labeled and a trained machine learning model is executed to remove at least a portion of the plurality of anatomical structures from images produced by one or more imaging modalities;

obtaining a number of initial patient images generated by at least one imaging modality of the one or more imaging modalities, wherein the number of initial patient images include the plurality of anatomical structures included in at least one body part of a patient, the at least one body part including a head region or a neck region of the patient;

executing the trained machine learning model with respect to the number of initial patient images to remove or highlight one or more anatomical structures of the plurality of anatomical structures in the number of initial patient images and produce a number of modified patient images that include at least one remaining anatomical structure of the plurality of anatomical structures; and rendering, based on the number of modified patient images, a number of views of the at least one remaining anatomical structure of the plurality of anatomical structures located in at least one of the head region or the neck region of the patient that are displayed via one or more computing devices.

2. The method of claim 1, wherein the plurality of anatomical structures include bone, tissue, blood vessels, plaque, or one or more combinations thereof.

3. The method of claim 2, wherein the one or more anatomical structures removed from the plurality of anatomical structures include bone, tissue, plaque, or one or more combinations thereof, and the at least one remaining anatomical structure includes one or more blood vessels.

4. The method of claim 1, wherein the number of views are predetermined views of one or more blood vessel segments and the predetermined views are accessible in response to input from a user of the one or more computing devices selecting one or more user interface elements corresponding to predetermined views.

5. The method of claim 4, wherein the predetermined views include one or more segments of the aortic arch, the Circle of Willis viewed from a plurality of perspectives, one or more segments of the left carotid artery viewed from a plurality of perspectives, one or more segments of the right carotid artery viewed from a plurality of perspectives, one or more segments of the (left/right) middle cerebral artery viewed from a plurality of perspectives, one or more segments of the (left/right) internal carotid artery viewed from a plurality of perspectives, one or more segments of the (left/right) external carotid artery viewed from a plurality of perspectives, one or more segments of the (left/right) anterior cerebral artery viewed from a plurality of perspectives, one or more segments of the (left/right) posterior cerebral artery viewed from a plurality of perspectives, one or more segments of the (left/right) vertebral artery viewed from a plurality of perspectives, one or more segments of the basilar artery viewed from a plurality of perspectives, one or more segments of one or more superior cerebral veins viewed from a plurality of perspectives, one or more segments of one or more inferior cerebral veins viewed from a plurality of perspectives, one or more segments of the superficial middle cerebral vein viewed from a plurality of perspectives, one or more segments of the superior anastomotic vein viewed from a plurality of perspectives, one or more segments of the inferior anastomotic vein viewed from a plurality of perspectives, one or more segments of one or more internal cerebral veins viewed from a plurality of perspectives, one or more segments of the basal veins of Rosenthal viewed from a plurality of perspectives, one or more segments of the basal veins, at least a portion of the great cerebral vein of Galen viewed from a plurality of perspectives, one or more segments of one or more superior cerebellar veins viewed from a plurality of perspectives, one or more segments of one or more inferior cerebellar veins viewed from a plurality of perspectives, one or more segments of one or more dural venous sinuses viewed from a plurality of perspectives, or one or more combinations thereof.

6. The method of claim 4, wherein the predetermined views include one or more maximum intensity projection views, one or more volume rendered views, one or more curved planar reformation views, or one or more combinations thereof.

7. The method of claim 6, wherein the one or more curved planar reformation views are generated by determining a centerline of at least one blood vessel included in the one or more curved planar reformation views.

8. The method of claim 4, comprising:

receiving additional input to cause at least a portion of the at least one remaining anatomical structure included in the number of modified patient images to be removed.

9. The method of claim 8, comprising:

generating, based on the additional input, one or more additional modified patient images that include views of fewer blood vessels than a number of blood vessels present in the number of modified patient images.

10. The method of claim 9, wherein the one or more additional modified patient images include at least one of a first view of first blood vessels included in a left hemisphere of a brain of the patient, a second view of second blood vessels included in a right hemisphere of the brain of the patient, a third view of third blood vessels included in an anterior region of the brain of the patient, and a fourth view of fourth blood vessels included in a posterior region of the brain of the patient.

11. The method of claim 1, wherein the one or more imaging modalities include computed tomography angiography (CTA), magnetic resonance angiography (MRA), tomographically-reconstructed digital subtraction angiography (DSA), or one or more combinations thereof.

12. The method of claim 1, wherein the number of views of the head region of the patient, the neck region of the patient, or both the head region and the neck region of the patient are modified to indicate one or more vessel characteristics that can include blood flow patterns, vessel curvature, vessel diameters, blood vessel wall shear stress, plaque, plaque type located in one or more vessels, stenosis grading, or one or more combinations thereof.

13. The method of claim 12, wherein values related to measurements of the one or more vessel characteristics are displayed as one or more overlays in the number of views according to one or more color schemes, one or more brightness schemes, or one or more shading schemes, the one or more color schemes, one or more brightness schemes, or one or more shading schemes being representative of differing values of the measurements of the one or more vessel characteristics.

14. The method of claim 1, wherein the number of views are used to determine a treatment plan for the patient with respect to a vessel abnormality.

15. The method of claim 14, wherein the number of views indicate one or more anatomical landmarks that can be used in determining the treatment plan for the patient.

16. The method of claim 1, comprising:

determining the number of views and an additional number of views for the patient over a period of time; and determining, based on the additional number of views, an amount of progression of a blood vessel-related physiological or abnormal condition, a response to treatment for the blood vessel-related physiological or abnormal condition, a relapse of the blood vessel-related physiological or abnormal condition, or guidance for treatment of the blood vessel-related physiological or abnormal condition.

17. The method of claim 16, wherein the number of views and the additional number of views of the patient are combined to generate one or more aggregate views that indicate changes to one or more vessel characteristics of the patient over the period of time, the one or more vessel characteristics including at least one of blood flow patterns, vessel curvature, vessel diameters, blood vessel wall shear stress, plaque, plaque type located in one or more vessels, or stenosis grading.

18. A system comprising:

one or more hardware processors; and memory storing computer-readable instructions that, when executed by the one or more hardware processors, cause the one or more hardware processors to perform operations comprising:

performing a training process for a machine learning model using training data that includes a number of training images, wherein a plurality of anatomical structures are labeled and a trained machine learning model is executed to remove at least a portion of the plurality of anatomical structures from images produced by one or more imaging modalities;

obtaining a number of initial patient images generated by at least one imaging modality of the one or more imaging modalities, wherein the number of initial patient images include the plurality of anatomical structures included in at least one of a head region or a neck region of a patient;

executing the trained machine learning model with respect to the number of initial patient images to remove or highlight one or more anatomical structures of the plurality of anatomical structures in the number of initial patient images and produce a number of modified patient images that include at least one remaining anatomical structure of the plurality of anatomical structures; and rendering, based on the number of modified patient images, a number of views of the at least one remaining anatomical structure of the plurality of anatomical structures located in at least one of the head region or the neck region of the patient that are displayed via one or more computing devices.

19. The system of claim 18, wherein the memory stores additional computer-readable instructions that, when executed by the one or more hardware processors, cause the one or more hardware processors to perform operations comprising:

analyzing, by a first machine learning architecture, the number of initial patient images to determine a first portion of the number of initial patient images corresponding to a first anatomical region of the patient and a second portion of the number of initial patient images corresponding to a second anatomical region of the patient, the first anatomical region and the second anatomical region corresponding to at least two of the head region, the neck region, or the aortic arch.

20. The system of claim 19, wherein:

the first machine learning architecture includes a neural network architecture; and the first machine learning architecture outputs a probability map indicating one or more probabilities of individual initial patient images corresponding to the first anatomical region, the second anatomical region, or both the first anatomical region and the second anatomical region.

21. The system of claim 20, wherein the memory stores additional computer-readable instructions that, when executed by the one or more hardware processors, cause the one or more hardware processors to perform operations comprising:

analyzing, by a second machine learning architecture and based on the probability map, the number of initial patient images to determine segmentation data for blood vessels included in the first anatomical region and the second anatomical region.

22. The system of claim 21, wherein the first machine learning architecture includes a residual neural network architecture and the second machine learning architecture includes at least one transformer-based machine learning architecture.

* * * * *